US006668653B2

(12) United States Patent
Kushibiki et al.

(10) Patent No.: US 6,668,653 B2
(45) Date of Patent: Dec. 30, 2003

(54) METHOD AND APPARATUS FOR MEASURING LSAW PROPAGATION CHARACTERISTICS

(75) Inventors: Jun-ichi Kushibiki, 2-71, Yamada-honcho, Taihaku-ku, Sendai-shi, Miyagi (JP), 982-0816; Yuu Ono, Miyagi (JP)

(73) Assignee: Jun-ichi Kushibiki, Miyagi (JP)

( * ) Notice: Subject to any disclaimer, the term of this patent is extended or adjusted under 35 U.S.C. 154(b) by 113 days.

(21) Appl. No.: 10/039,705

(22) Filed: Oct. 19, 2001

(65) Prior Publication Data
US 2002/0075758 A1 Jun. 20, 2002

(30) Foreign Application Priority Data
Oct. 20, 2000 (JP) ......................................... 2000-320932

(51) Int. Cl.[7] ............................................... G01N 29/04

(52) U.S. Cl. .......................................... 73/606; 73/602

(58) Field of Search ........................ 73/588, 605, 607, 73/608, 606, 602, 618, 619, 620, 627, 628, 629; 702/33, 39, 189

(56) References Cited

U.S. PATENT DOCUMENTS

| 4,254,660 A | | 3/1981 | Prause |
| 4,503,708 A | * | 3/1985 | Kino et al. .................... 73/628 |
| 4,541,281 A | * | 9/1985 | Chubachi et al. ............. 73/606 |
| 5,406,849 A | * | 4/1995 | Drescher-Krasicka et al. ........................... 73/606 |

FOREIGN PATENT DOCUMENTS

JP      28163499      10/1999

OTHER PUBLICATIONS

J. Kushibiki et al.: "Experimental Considerations on Water-Couplant Temperature for Accurate Velocity Measurements by the LFB Ultrasonic Material Characterization System" IEEE Ultrasonics Symp., 2000. Proc.

Kroebel W Et Al: "Recent Results Of Absolute Sound Velocity Measurements In Pure Water And Sea Water At Atmospheric Pressure" Acustica, S. Hirzel Verlag Stuttgart, DE, vol. 3B, No. 3, Jun. 1976, pp 154–164.

Kobayashi, T., et al: "Improvement of measurement accuracy of line-focus beam acoustic microscope system," Ultrasonics Symposium, 1992 Proc., IEEE 1992 Tucson, AZ, ,IEEE, Oct. 20, 1992, pp 739–742.

Kushibiki J–I et al: "Material Characterization By Line-Focus–Beam Acoustic Microscope" IEEE Transactions On Sonics And Ultrasonics, Ieee Inc. New York, US, vol. SU–32, No. 2, Mar. 1985, pp. 189–212.

(List continued on next page.)

Primary Examiner—Helen Kwok
(74) Attorney, Agent, or Firm—David N. Lathrop, Esq.; Gallagher & Lathrop

(57) ABSTRACT

The temperature distribution in water is measured by two thermocouples to obtain a temperature compensating parameter. Under measurement conditions where the temperature distribution in water varies, a measured V(z) curve is used to monitor a change in the wave number of a longitudinal wave in an ultrasonic wave propagation region in water to thereby detect variations in the water temperature and the longitudinal wave velocity with high accuracy.

27 Claims, 23 Drawing Sheets

OTHER PUBLICATIONS

Kushibiki J–I Et Al: "A Method For Calibrating The Line-Focus–Beam Acoustic Microscopy System" IEEE Transactions On Ultrasonics, Ferroelectrics & Freq. Control, IEEE, NY, vol. 45, no 2, Mar. 1, 1998 pp 421–430.

J. Kushibiki and N. Chubachi, "Material characterization by line–focus–beam acoustic microscope," IEEE Trans. Sonics and Ultrason., vol. SU–32, pp. 189–212 (1985).

W. Kroebel and K. –H. Mahrt, "Recent results of absolute sound velocity measurements in pure water and sea water at atmospheric pressure," Acustica, vol. 35, pp. 154–164 (1976).

J. Kushibiki, Y. Ono, and I. Takanaga, "Ultrasonic micro–spectroscopy of LiNbO3 and LiTaO3 single crystals for SAW devices," Trans. IEICE C–I, vol. J82–C–I, pp. 715–727 (1999).

J. Kushibiki and M. Arakawa, "A method for calibrating the line–focus–beam acoustic microscopy system," IEEE Trans. Ultrason., Ferroelect., Freq. Contr., vol. 45, pp. 421–430 (1998).

* cited by examiner

- S1: LOAD V(z) DATA
- S2: CALCULATE $V_I'(z) = V(z) - V_L'(z)$
- S3: REMOVE SPRIOUS BY DIGITAL FILTERING
- S4: SYNTHESIZE $\Delta V_L(z)$ FROM $V_I'(z)$ BY DIGITAL FILTERING
- S5: $V_I(z) = V_I'(z) - \Delta V_L(z)$
- S6: PERFORM FFT ON $V_I(z)$ TO OBTAIN $\Delta z$
- S7: OBTAIN $V_W$ FROM $T_W$ BASED ON REFERENCE (3)
- S8: CALCULATE $V_{LSAW}$ FROM $\Delta z$ AND $V_W$ ACCORDING TO EQUATION (6)

1: Teflon  4: LiNbO$_3$  7: Si
2: Pyrex glass  5: Quartz  8: Al
3: LiTaO$_3$  6: GGG  9: Au ic parameters such as phase velocity and propagation attenuation of LSAW with high accuracy. Further, a measurement reproducibility of $\pm 0.002\%$ ($\pm 1$ppm) is excellent...

METHOD AND APPARATUS FOR MEASURING LSAW PROPAGATION CHARACTERISTICS

BACKGROUND OF THE INVENTION

The present invention relates to a method for highly accurate measurements of propagation characteristics, in particular, phase velocity, of leaky surface acoustic waves (LSAWs) by an ultrasonic material characterization system using a focused ultrasonic beam.

The ultrasonic material characterization system has been developed as a new substance/material property analysis/evaluation technique, and it uses ultrasonic plane waves and ultrasonic focused waves for quantitative measurements. One of the quantitative measurement schemes using the ultrasonic focused waves is a V(z) curve analysis. This scheme is to measure propagation characteristics (phase velocity and propagation attenuation) of leaky surface acoustic waves (LSAWs) excited on a water-loaded specimen surface. The measurement can be done using an ultrasonic point-focus beam (PFB) and an ultrasonic line-focus beam (LFB). Now, a description will be given of an LFB ultrasonic material characterization system (see References (1) and (2)).

The LFB ultrasonic material characterization system determines LSAW propagation characteristics on the water/specimen boundary through analysis of a V(z) curve obtained by changing the relative distance z between an LFB ultrasonic device and the specimen. The principle of measurement by the LFB ultrasonic material characterization system will be described with reference to FIG. 1, which depicts in section the system wherein an ultrasonic device composed of an ultrasonic transducer 1 and an LFB acoustic lens 2 and a specimen 4 are disposed. The coordinate system is defined with its origin at the focal point of the acoustic lens 2 in water 3 as shown. Ultrasonic plane waves excited by the ultrasonic transducer 1 are converged by the LFB acoustic lens in wedge form onto the surface of the specimen 4 through the water 3 used as a coupler. When the specimen 4 is moved away from a focal plane 5 toward the ultrasonic device, only those components of the reflected wave from the specimen 4 which propagate through the acoustic lens 2 along paths #0 and #1 approximately shown in FIG. 1 most contribute to the generation of the output from the ultrasonic transducer 1 due to the effect of the cylindrical surface of the acoustic lens 2. The component #0 is a directly reflected component from the specimen 4, and this component will hereinafter be referred to as a phasor $V_0(z)$. On the other hand, the component #1 is one that impinges on the specimen 4 at an LSAW excitation critical angle $\theta_{LSAW}$ and propagates as an LSAW on the surface of the specimen 4—this component will hereinafter be referred to as a phasor $V_1(z)$. The phasors are given by the following equations (1) and (2) taking into account their phase and amplitude variations with the lengths z of their paths.

$$V_0(z)=|V_0(z)|\exp\{j(-2k_W z+\phi_0)\} \quad (1)$$

$$V_1(z)=|V_1(z)|\exp\{j(-2k_W \cos\theta_{LSAW} z+\phi_1)\} \quad (2)$$

$$k_W=2\pi f/V_W \quad (3)$$

where $k_W$ and $V_W$ are the wave number and velocity of a longitudinal wave in the water 3, f is an ultrasonic frequency, and $\phi_0$ and $\phi_1$ are initial phases of the phasors. The transducer output V(z) is given by the following equation as the sum of the two phasors.

$$V(z)=V_0(z)+V_1(z) \quad (4)$$

Noting the amplitude of the transducer output signal, the amplitude V(z) of the phasor V(z) is given by the following equation (5).

$$V(z)=|V(z)|=|V_0(z)+V_1(z)| \quad (5)$$

Therefore, the V(z) curve takes a waveform that is periodically maximized and minimized due to variations in the relative phase difference between the two phasors with the distance z, and the interference interval $\Delta z$ of the V(z) curve is given by the following equation (6).

$$\Delta z=2\pi/k(\Delta z)=2\pi/2k_W(1-\cos\theta_{LSAW}) \quad (6)$$

where $k(\Delta z)$ is the wave number of the V(z) curve interference waveform on the V(z) curve. The LSAW velocity $V_{LSAW}$ is determined by the following equation (7) from the interference interval $\Delta z$ of the V(z) curve.

$$V_{LSAW}=\frac{V_W}{\sqrt{1-\left(1-\frac{V_W}{2f\Delta z}\right)^2}} \quad (7)$$

The LSAW propagation attenuation is also obtainable from the waveform attenuation factor of the V(z) curve.

FIG. 2 is a graph showing an example of the V(z) curve measured at an ultrasonic frequency f=225 MHz for a (111) GGG (Gadolinium Gallium Garnet) specimen with LSAWs propagating in the [$\overline{11}2$] direction.

A description will be given below of the procedure for the analysis of the V(z) curve to determine the LSAW velocity $V_{LSAW}$. FIG. 3 is a flowchart explaining the procedure for the V(z) curve analysis. Usually, the V(z) curve measured on a decibel scale (FIG. 4A) is converted to digital form and then read into a computer, wherein it is converted to a linear scale (step S1). A $V_L'$ curve, which is an approximation of a $V_L(z)$ curve reflecting the characteristic of the ultrasonic device, is subtracted from the V(z) curve to obtain a $V_I'(z)$ curve (step S2). The $V_L'(z)$ curve used in this case is, for example, such a V(z) curve as depicted in FIG. 4B which was measured for a Teflon (trademark) specimen in which no leaky surface acoustic waves are excited.

The next step is to remove, by digital filtering, small interference components (on the V(z) curve in FIG. 4A) due to a spurious noise signal caused on the $V_I'(z)$ curve by a carrier leakage signal in an RF switching circuit for generating an RF tone burst signal used in the measurement system or multiple-reflected signals of ultrasonic waves in the acoustic lens (step S3). After this, interference components (interference interval $\Delta z$ components) resulting from leaky surface acoustic waves are removed by digital filtering from the $V_I'(z)$ curve to synthesize a $\Delta V_L(z)$ curve representing low-frequency components including DC components (step S4). This is followed by subtracting $\Delta V_L(z)$ from $V_I'(z)$ calculated in step S2 to obtain such a $V_I(z)$ curve as shown in FIG. 5A which is an interference output necessary for analysis (step S5).

The digital filtering is implemented, for example, by the moving average method. An FFT analysis of the $V_I(z)$ curve provides such a frequency spectrum distribution as depicted in FIG. 5B, and the interference interval $\Delta z$ is obtained from the peak frequency (step S6). Since the longitudinal wave velocity $V_W$ in water is known as a function of temperature as set forth in Reference (3), it can be determined from the water temperature $T_W$ measured at the same time as the V(z) curve is measured (step S7). Therefore, the LSAW velocity $V_{LSAW}$ can be calculated by Eq. (7) from the interference interval $\Delta z$ and the longitudinal wave velocity $V_W$ (step S8). While in the above the analysis scheme has been described on the assumption of only one leaky surface acoustic wave mode, it is a matter of course that when multiple modes are present, propagation characteristics can be measured for each mode. The V(z) curve in FIG. 2 is shown to have removed therefrom by the moving average method the small interference components based on the above-mentioned spurious noise signal. Thus it can be seen that the $V_{LSAW}$ measurement accuracy depends mainly on the water temperature measurement accuracy, which determines the longitudinal wave velocity $V_W$, and the translation accuracy of a Z (vertical translation) stage used in the system.

Now, a description will be given of the influence of a temperature measurement error on the $V_{LSAW}$ measurement accuracy. FIG. 6 shows LSAW velocity measurement errors calculated by Eq. (7) with respect to water temperature measurement errors at LSAW velocities of 2000 m/s, 3000 m/s, 4000 m/s, 6000 m/s and 10000 m/s in a ±0.2° C. measurement error range with the true value of water temperature set to 23° C. From FIG. 6, it is shown that the LSAW velocity measurement with a resolution of, for example, ±0.002% requires the water temperature to be measured with an accuracy of ±0.02° C. Incidentally, when the water temperature is 23° C. or so, the longitudinal wave velocity linearly changes with temperature, and the rate of change is 2.83 (m/s)/° C.

FIG. 7 depicts in block form the LFB ultrasonic material characterization system. The coordinate axes x, y and z of the system are set as shown. An RF tone burst signal 7 from a transmitter 6A in a pulse mode measurement system 6, which is electrical circuitry, is converted by the ultrasonic transducer 1 to an ultrasonic signal. The ultrasonic signal is converged by the LFB acoustic lens 2 having a cylindrical surface into wedge form for incidence on the specimen 4 through the water 3. The reflected signal from the specimen surface is converted again by the transducer 1 to an electrical signal. The converted output from the transducer 1 is provided via a directional bridge 8 to and detected by a receiver 6B in the pulse mode measurement system 6, and the detected output is converted by an A/D converter 9 to an amplitude V(z) signal or complex V(z) signal in digital form, which is stored on a data recording medium (not shown) in a computer 14.

The amplitude (in the amplitude V(z) curve measurement mode), or amplitude and phase (in the complex V(z) curve measurement mode) of the transducer output V(z) are recorded as a function of the distance z between the specimen 4 and the acoustic lens 2 while at the same time bringing the former closer to the latter relative to the focal point of the lens 2 by driving a Z stage (not shown) in a mechanical stage 12. At this time, the distance z of translation of the Z stage is measured by a laser interferometer 15, from which pulses synchronized with the translation of the Z stage are fed to the A/D converter 9. At the same time, the temperature of the water 3 is measured using a thermocouple 10 and a digital voltmeter 11.

The mechanical stage 12 comprises, in addition to the Z stage, a θ (rotation) stage for measuring the dependence of LSAW propagation characteristics on the direction of propagation, an XY (horizontal translation) for measuring the distribution of LSAW velocity on the specimen surface, a tilting stage for accurate alignment between the ultrasonic device and the specimen 4, and a specimen holder provided with a vacuum-suction mechanism for firmly holding thereon the specimen 4. The XY stage, the Z stage, the θ stage and the tilting stage for alignment use are each driven by a motor and placed under the control of a stage controller 13. To provide a highly stabilized temperature-measuring environment, the mechanical stage including the specimen is placed in a temperature-controlled chamber 16. The characterization system is further provided with a pure water supply/drain system 17 and a specimen loader/unloader 18 to permit supply and drain of the water 3 and replacement of the specimen 3 without opening the door of the temperature-controlled chamber 16 and hence under stabilized temperature conditions. The computer 14 controls the entire system and measures and analyzes the V(z) curve to determine the LSAW propagation characteristics.

The thermocouple 10 is disposed as close to the ultrasonic wave propagation region as possible as depicted in FIG. 7 since it cannot be directly inserted into the ultrasonic wave propagation region during measurement. In general, however, a temperature distribution exists in the water 3. This is attributable mainly to a temperature gradient in the water 3 by a temperature drop in the vicinity of the water surface due to the heat of evaporation of the water and variations in the temperature environment around the water 3 by the flow of air. On this account, the water temperature directly below the cylindrical surface of the acoustic lens 2 more or less differs from the temperature measured by the thermocouple 10. This difference becomes an error in estimating the longitudinal wave velocity $V_W$, constituting a leading factor in decreasing the accuracy in measuring the LSAW velocity. Hence, stabilization of the temperature environment in the neighborhood of the specimen is extremely important in measuring the water temperature with high accuracy, that is, measuring the LSAW velocity with high accuracy.

For the reasons given above, the entire system is installed in a temperature-controlled room, or the entire mechanical stage including the specimen is placed in a temperature-controlled chamber to stabilize the temperature environment for measurements so as to provide increased accuracy in measuring the LSAW velocity. Moreover, it is already known in the art that when the ultrasonic device and the portion surrounding the specimen are placed in a closed or semi-closed space to minimize the flow of air to keep the atmosphere around the water supersaturated, the temperature distribution in the water is reduced to further stabilize the measurement temperature environment. In the temperature environment thus stabilized, a measurement repeatability of ±0.002% is attained at one fixed point on the specimen surface (see References (2) and (4)). Further, there has been proposed a method that uses a standard specimen to calibrate a temperature measurement error due to the temperature distribution in the water 3, an error in the travel of the Z stage, and an error in the absolute value of the LSAW velocity measured value owing to the frequency characteristic of the ultrasonic device used (see Reference (5)).

However, when the measurement extends over a long time (an hour or longer, for instance), the quantity of water 3 decreases due to evaporation, causing changes in the LSAW velocity measured. It is considered that this is because the water temperature distribution differs with the quantity of water. And in measurement of a two-dimensional distribution of the LSAW velocity, the measurement resolution is lower than in the measurement at one fixed point. The reason for this is considered that the temperature distribution in the water varies with a change in the temperature distribution throughout the specimen surface according to the position of placement of the specimen on the specimen holder, or a change in the temperature environment around the specimen by the translation of the XY stage in the measurement of the two-dimensional distribution of the LSAW velocity. The above-mentioned absolute calibration method using the standard specimen is based on the assumption that the specimen under measurement and the standard specimen are equal in the temperature distribution in the water, but it is not clear to which extent their temperature distributions actually agree with each other. Further, it is still unclear how much the temperature distribution in the water changes with a decrease in the quantity of water or the translation of the XY stage. Besides, it is considered that the temperature distribution in the water and its variation differ with the quantity and surface configuration of water, the kind and shape of the specimen, the measurement temperature environment, measurement conditions, the ultrasonic device configuration, or the system used.

As described above, it is not clear in the prior art what temperature distribution in the water is, and consequently, it is also unclear how the water temperature distribution affects the accuracy of the LSAW velocity measurement. In addition, under measurement conditions where the temperature difference in the water varies during measurement as in the case of measuring the two-dimensional distribution of the LSAW velocity or carrying out the measurement for a long time, it is impossible to remove errors in the LSAW velocity measurement due to the variation in the water temperature difference. Hence, the measurement accuracy of the system is insufficient to detect slight variations in elastic properties of highly homogeneous single-crystal substrates now widely used as electronic device materials.

SUMMARY OF THE INVENTION

It is therefore an object of the present invention to provide an LSAW propagation characteristics measuring method and apparatus that correct an error in the water temperature measurement caused by the temperature distribution in the water to provide increased accuracy in the LSAW velocity measurement for high-precision analysis and evaluation of material properties.

According to this invention method for high-precision measurement of LSAW propagation characteristics by the ultrasonic material characterization system, a temperature compensating parameter is obtained by pre-measuring, with a thermocouple or similar temperature measuring element, the temperature distribution in the water at one fixed point on the specimen surface under sufficiently stable water temperature conditions, and the value of temperature measured in a temperature monitoring region during the V(z) curve measurement is corrected or compensated for by the temperature compensating value to thereby detect the temperature in the ultrasonic wave propagation region with high accuracy.

Under measurement conditions where the water temperature distribution varies as in the measurement of the two-dimensional distribution of the LSAW velocity, the measured complex V(z) curve or amplitude V(z) curve is used to measure the wave number $k_W$ of the longitudinal wave in the ultrasonic wave propagation region, from which are obtained variations in the temperature of the propagation region and in the longitudinal wave velocity. More specifically, in an apparatus that has amplitude and phase measuring functions and is capable of measuring the complex V(z) curve, the wave number $k_W$ is obtained through utilization of the directly reflected signal (phasor $V_0(z)$) from the specimen that propagates near the center axis of the acoustic lens to form the V(z) curve. Alternatively, phase information of the V(z) curve is used to obtain the wave number $k_W$ of the longitudinal wave.

In an apparatus that has no phase measuring function but is capable of measuring only the amplitude V(z) curve, the wave number $k_W$ is obtained through utilization of the interference between a carrier leakage signal in the RF switching circuit for generating an RF tone burst signal and the V(z) signal. Alternatively, the wave number $k_W$ is obtained with an electric interference method that causes interference between a continuous wave reference signal and the V(z) signal. Furthermore, the wave number $k_W$ thus obtained is used to precisely detect a temperature variation in the measurement of the two-dimensional distribution of the LSAW velocity with reference to the temperature at one fixed point on the specimen surface pre-measured under the stable temperature condition, and the thus obtained temperature variation is used to detect a change in the longitudinal wave velocity to eliminate an error in the LSAW velocity measurement.

Thus, the LSAW velocity can be measured with high accuracy even under the measurement conditions where the temperature distribution in the water varies.

DETAILED DESCRIPTION OF THE PREFERRED EMBODIMENTS

Figure 8:
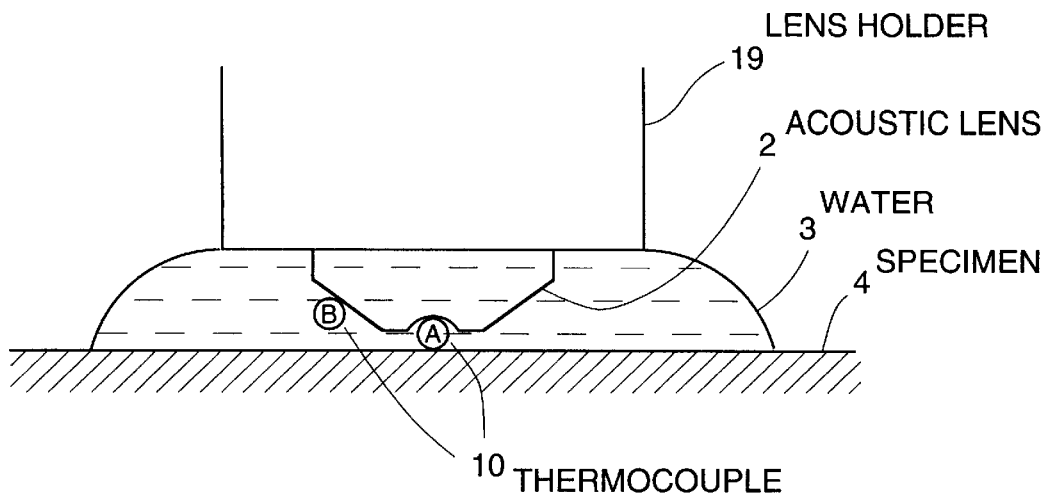
FIG. 8 is a schematic diagram indicating the positions of thermocouples for measuring the water temperature distribution.

A description will be given first of the procedure for accurately measuring the water temperature in the ultrasonic wave propagation region at one fixed point on the specimen surface. As depicted in FIG. 8, thermocouples 10 are inserted in a region A directly below the cylindrical surface of the acoustic lens 2 in which a wedge-shape-focused ultrasonic wave propagates, and a region B near the acoustic lens 2 where to monitor the water temperature during the V(z) curve measurement. And, under conditions of stable temperature distribution in the water 3 the temperature $T_A$ in the region A and the temperature $T_B$ in the region B are measured at the same time. As a result, the temperature difference $\Delta T$ between the two points (a temperature compensating parameter) is obtained by Eq. (8). With the use of the temperature compensating parameter $\Delta T$, the temperature $T_A$ in the region A during the V(z) curve measurement under conditions of sufficiently stable water temperature can be calculated by Eq. (9) from the temperature $T_B$ in the region B.

$$\Delta T = T_A - T_B \quad (8)$$

$$T_A = T_B + \Delta T \quad (9)$$

Figure 9:
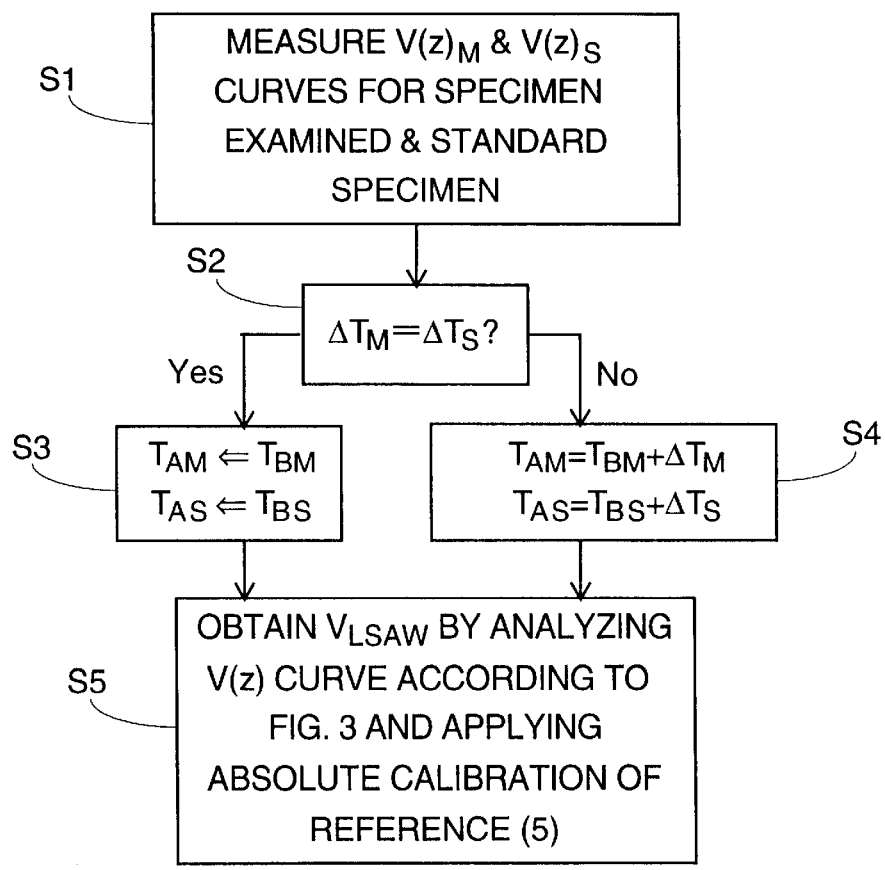
FIG. 9 is a flowchart showing a method by which an error in the measurement of temperature at one fixed point on the specimen surface under the sufficiently stable temperature condition during the LSAW velocity measurement is removed to obtain the LSAW velocity with high accuracy.

FIG. 9 is a flowchart of the procedure by which temperature compensating parameters $\Delta T_M$ and $\Delta T_S$ pre-measured for a specimen under examination and a standard specimen for system calibration are used to remove a temperature measurement error in the measurement and analysis of the V(z) curve to obtain the LSAW velocity for the specimen under examination. The procedure begins with measuring $V(z)_M$ and $V(z)_S$ curves for the specimen under examination and the standard specimen at single points on the specimen surfaces under sufficiently stable temperature conditions. In this instance, the measured V(z) curve is FFT-analyzed by the method described later on to obtain the wave number of the longitudinal wave in the ultrasonic wave propagation region in the water. The V(z) curve is measured repeatedly until the wave number value becomes stable within a predetermined range. This is intended to make sure that the water temperature is stable (step S1). The temperature differences $\Delta T_M$ and $\Delta T_S$ for the specimen under examination and the standard specimen are compared to see if they are equal (step S2). In the case where the respective measurements are carried out under substantially the same conditions such as the temperature environment around the specimen and the quantity of water and the temperature differences $\Delta T_M$ and $\Delta T_S$ are equal, each measurement value, including an error by the temperature difference $\Delta T$, too, is calibrated by absolute calibration in step S5 described later on. Therefore, in this instance, no temperature compensation is made and respective temperature measurement values $T_{BM}$ and $T_{BS}$ are set as water temperatures $T_{AM}$ and $T_{AS}$ during measurements of the specimen under examination and the standard specimen (step S3).

Figure 3:
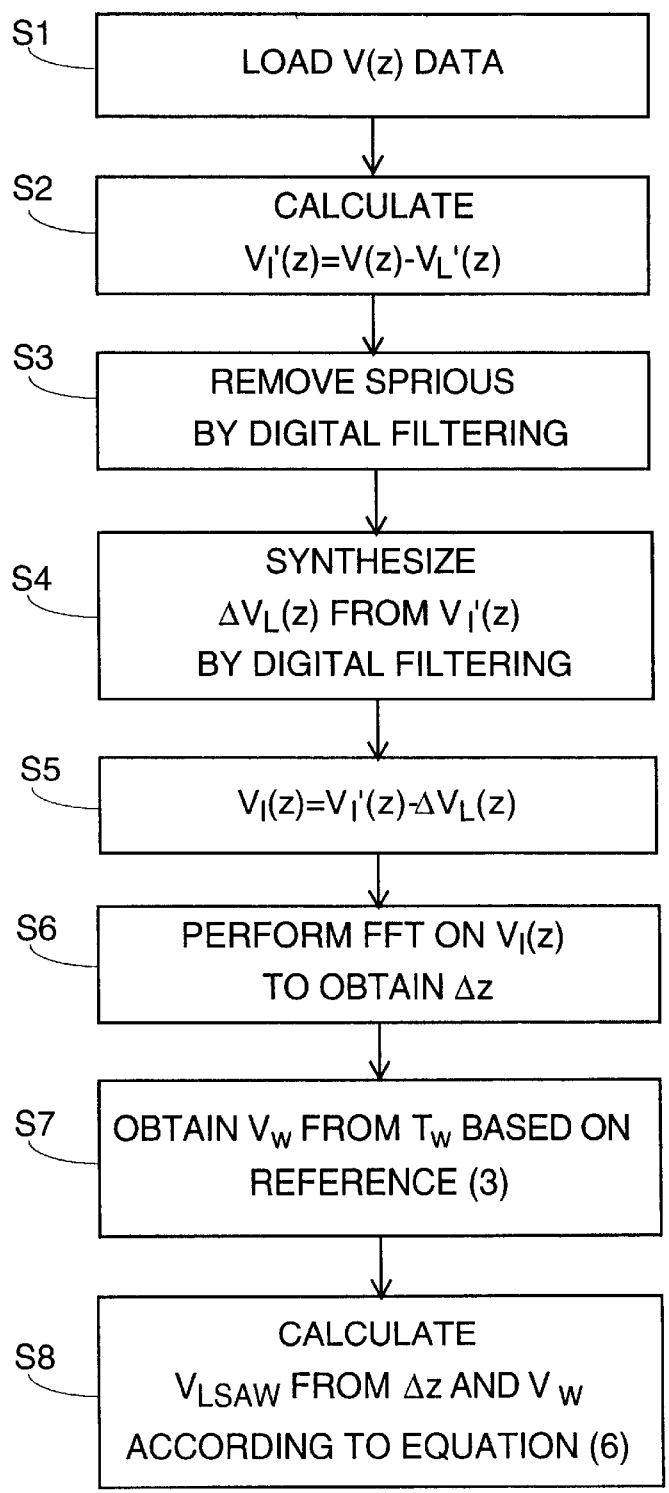
FIG. 3 is a flowchart showing a V(z) curve analysis scheme.

The next step is to obtain the leaky surface acoustic wave propagation velocity $V_{LSAW}$ by the V(z) curve analysis described previously in respect of FIG. 3 and the absolute calibration disclosed in Reference (5) (step S5). This facilitates exclusion of the influence of the water temperature measurement error in the LSAW velocity measurement, ensuring accurate detection of the LSAW velocity $V_{LSAW}$.

On the other hand, in the case where the measurement conditions for the specimen under examination and the standard specimen differ more or less and the temperature differences $\Delta T_M$ and $\Delta T_S$ differ in step S2 in FIG. 9, the values $T_{AM}$ and $T_{AS}$ are set as water temperatures for respective measurements of the both specimens (step S4). The values $T_{AM}$ and $T_{AS}$ are those obtained for the specimen under examination and the standard specimen by correcting or compensating for the temperature measurement values $T_{BM}$ and $T_{BS}$ with the temperature compensating parameters $\Delta T_M$ and $\Delta T_S$ by Eq. (9). This is followed by the analysis of the V(z) curve and the absolute calibration to obtain the LSAW propagation velocity $V_{LSAW}$ (step S5). Even when the temperature differences $\Delta T_M$ and $\Delta T_S$ differ, if the estimated error is within a predetermined range, the LSAW propagation velocity can be measured by the absolute calibration in step S5 after step S3 without making any temperature compensation in step S4.

Figure 2:
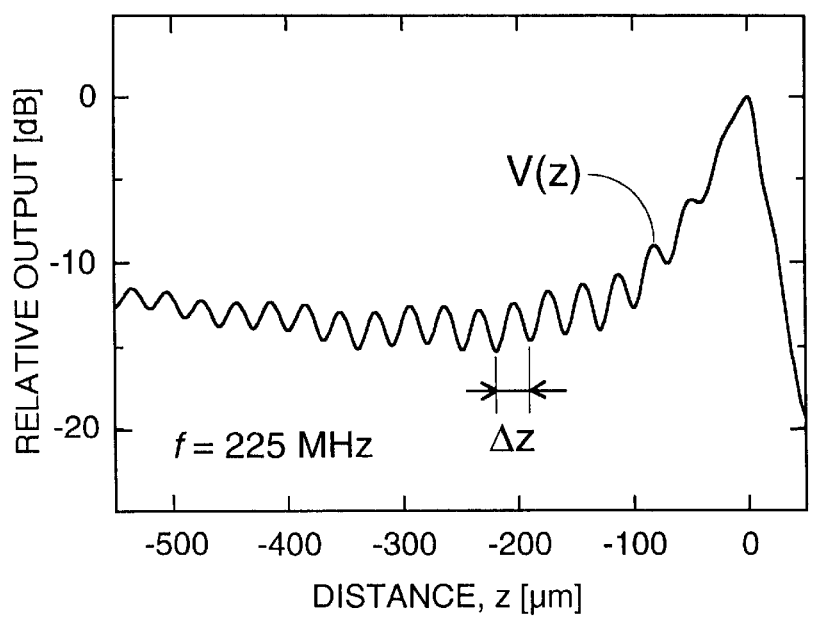
FIG. 2 is a graph showing the V(z) curve.

A brief description will be given of the absolute calibration method set forth in Reference (5). The first step is to obtain a theoretical value of the LSAW propagation velocity calculated from the elastic constant of a bulk standard specimen (as of GGG single crystal) obtained from the sound velocity and density actually measured for the specimen at a temperature set to a constant value. Then, a value corresponding to the interference interval $\Delta z$ of the V(z) curve (see FIG. 2) is obtained by Eq. (7), as $\Delta z_S$(calc), using the ultrasonic frequency f used for the measurement of the LSAW propagation velocity in the apparatus of FIG. 7 and the sound velocity $V_W$ in the water at the above-mentioned measurement temperature (mentioned in Reference (3)). Further, $\Delta z_S$ (meas) is obtained from the V(z) curve, $V(z)_S$, measured for the standard specimen. These values are used to obtain a calibration coefficient $K=\Delta z_S$(calc)$/\Delta z_S$(meas). In the present invention, the measured values of the ultrasonic wave propagation velocities (longitudinal wave velocity) $V_W$ in the water at respective temperatures based on Reference (3) are prestored as a table in the computer 14 in FIG. 7, from which the propagation velocity $V_W$ corresponding to the measurement temperature is read out as required.

The next step is to obtain a calibrated value $\Delta z_M$ as $\Delta z_M = K\Delta z_M$(meas) from $\Delta z_M$(meas) calculated from the V(z) curve, $V(z)_M$, measured for the specimen under examination. The calibrated value $\Delta z_M$ and the acoustic velocity $V_W$ at the water temperature $T_W$ are substituted into Eq. (7) to obtain an absolutely calibrated value $V_{LSAW}$.

When $\Delta T_M$ and $\Delta T_S$ differ in step S2, the value $V_{LSAW}$ is calculated in step S5 as described below. In the first place, the theoretical value $V_{LSAW}$ at the water temperature $T_{AS}=T_{BS}+\Delta T_S$ for the bulk standard specimen is calculated in the same manner as described above, and $\Delta z$ in Eq. (7) is calculated as the theoretical value $\Delta z_S$(calc) from the value $V_{LSAW}$, the acoustic velocity $V_W$ at the water temperature $T_{AS}$ and the frequency f. Further, $\Delta z_S$ (meas) is obtained from the V(z) curve, $V(z)_S$, measured for the standard specimen. These values are used to obtain the calibration coefficient $K=\Delta z_S$(calc)$/\Delta z_S$(meas). The next step is to obtain the calibrated value $\Delta z_M$ as $\Delta z_M=K\Delta z_M$(meas) from $\Delta z_M$(meas) obtained from the V(z) curve, $V(z)_M$, measured for the specimen under examination. The calibrated value $\Delta z_M$ and the longitudinal wave velocity $V_W$ in the water corresponding to the water temperature $T_{AM}=T_{BM}+\Delta T_M$ in the table are substituted into Eq. (7) to obtain the absolutely calibrated value $V_{LSAW}$.

Incidentally, when the water temperature distribution varies with the translation of the XY stage as in the measurement of the two-dimensional velocity distribution, the temperature difference $\Delta T$ is not always constant. In view of this, the wave number $k_W$ of the longitudinal wave in the water is obtained from the measured V(z) curve, and is used to estimate the temperature and variations in the longitudinal wave velocity in the measurement region to thereby calculate the ultrasonic wave propagation velocity $V_W(x, y)$ in the water at a given position (x, y). This permits highly accurate measurement of the LSAW propagation velocity.

Figure 10A:
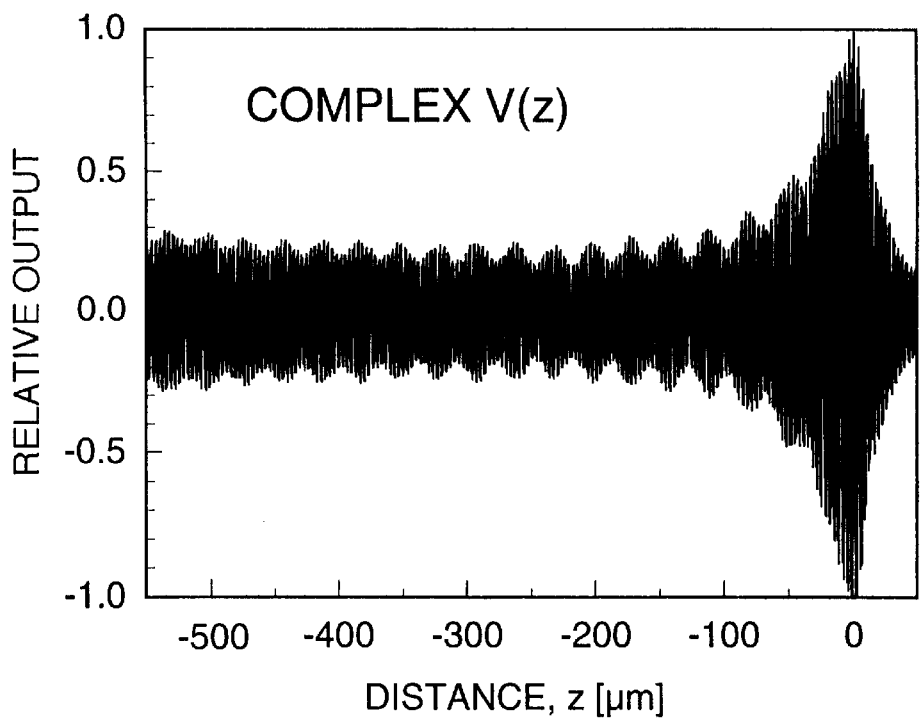
FIG. 10A is a graph showing a complex V(z) curve represented by imaginary and real parts.
Figure 10B:
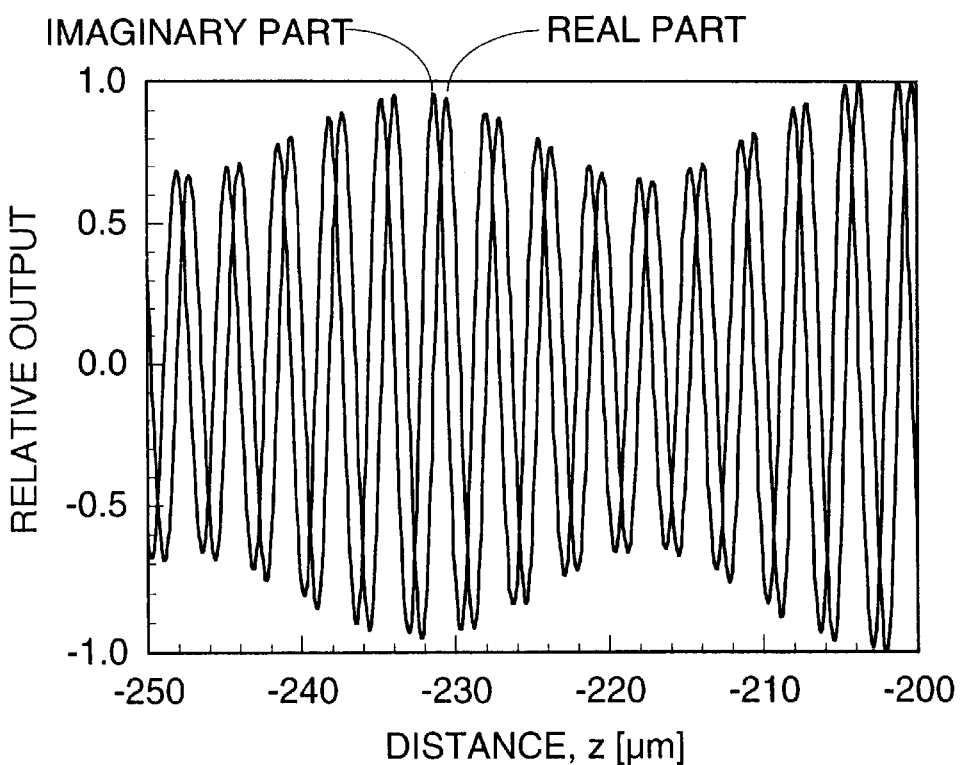
FIG. 10B is a graph showing, on an enlarged scale, the waveform of the complex V(z) curve in a region z=−250 μm to −200 μm in FIG. 10A.
Figure 11:
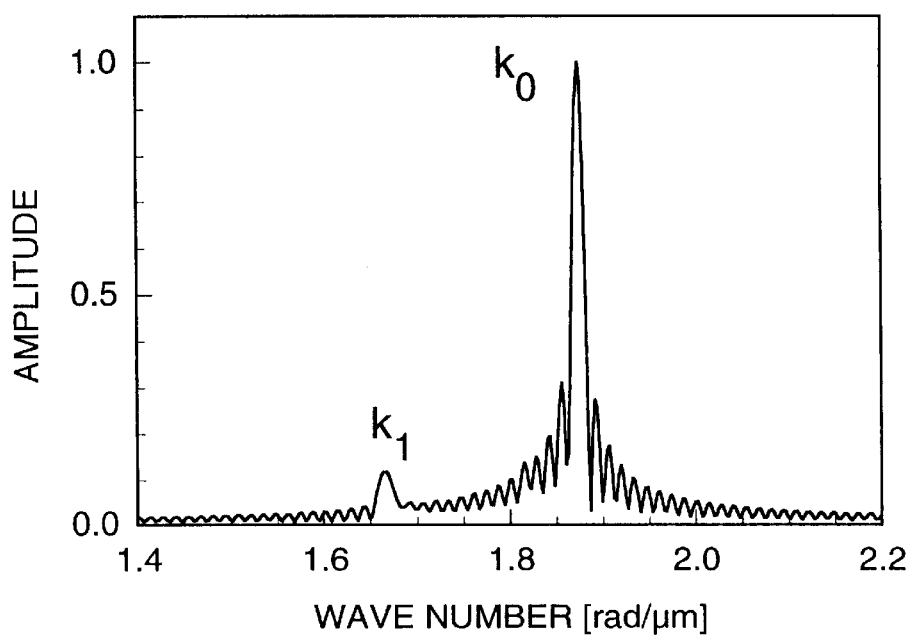
FIG. 11 is a graph showing a spectrum distribution obtained by an FFT analysis of the waveform of the complex V(z) curve in a region z=−500 μm to −30 μm in FIG. 10A.

Several methods for calculating the wave number $k_W$ of the longitudinal wave from the measured V(z) curve will be described below. A description will be given first of the procedure for calculating the wave number $k_W$ from the complex V(z) curve. As referred to previously, the ultrasonic transducer output V(z) is composed of the phasor $V_0(z)$ that is a directly reflected signal from the specimen and the phasor $V_1$ that is a signal propagating as the leaky surface acoustic wave LSAW along the specimen surface. FIG. 10A shows an example of the complex V(z) curve measured for a (111) GGG specimen at the ultrasonic frequency f=225 MHz. The direction of LSAW propagation is the same as in the case of FIG. 2. FIG. 10B is an enlarged diagram showing the waveform in a region z=−250 $\mu$m to −200 $\mu$m in FIG. 10A, from which it can be seen that the complex V(z) curve is expressed by real and imaginary parts. FIG. 11 depicts a frequency spectrum distribution obtained by an FFT analysis of the waveform of the complex V(z) curve in the range of z=−500 $\mu$m to −30 $\mu$m. The spectral distribution has two peaks corresponding to the wave number $k_0(=2k_W)$ for z of the phasor $V_0(z)$ expressed by Eq. (1) and the wave number $k_1(=2k_W \cos\theta_{LSAW})$ for z of the phasor $V_1(z)$ expressed by Eq. (2). Therefore, the wave number $k_W$ is obtained from $k_W=k_0/2$ based on the former $k_0$.

Figure 1:
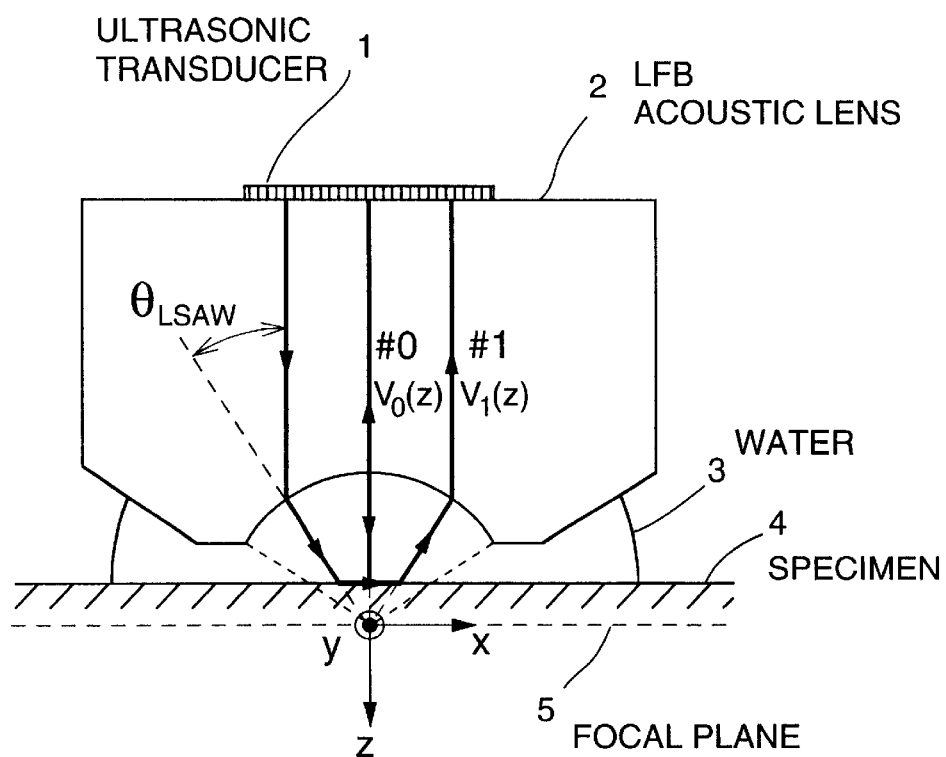
FIG. 1 is a schematic diagram for explaining the principle of generation of a V(z) curve.

Next, a method for obtaining the wave number $k_W$ from the amplitude V(z) curve will be described below. The RF tone burst signal generator yields a carrier leakage signal at the time of generating the RF tone burst signal. The carrier leakage signal is sent to the acoustic system (ultrasonic device/acoustic coupler (water)/specimen) together with the RF tone burst signal and is mostly reflected off at the input electric terminal of the ultrasonic transducer, and is received along with the reflected signal from the specimen. Accordingly, the component forming the transducer output includes a phasor $V_e$ based on the carrier leakage signal, in addition to the phasors $V_0(z)$ and $V_1(z)$ depicted in FIG. 1. The phasor $V_e$ is not dependent on the relative distance z between the acoustic lens and the specimen and is approximately expressed by the following equation (10).

$$V_e = |V_e \exp(j\phi_e)| \tag{10}$$

where $\phi_e$ is the phase of the phasor $V_e$. Accordingly, the amplitude V(z) of the ultrasonic transducer output, taking into account the phasor $V_e$, is expressed by the following equation (11).

$$V(z) = |V(z) + V_e| = |V_0(z) + V_1(z) + V_e| \tag{11}$$

Figure 4A:
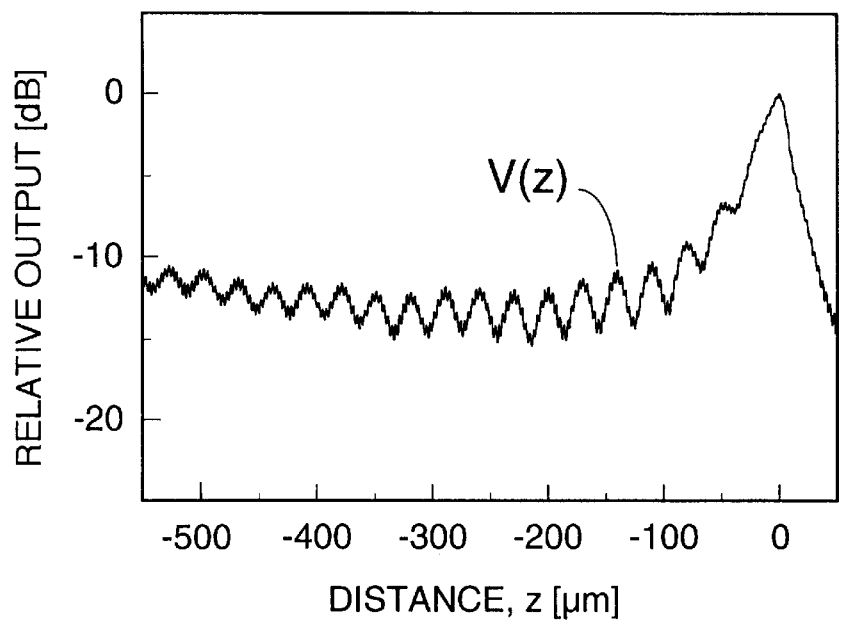
FIG. 4A is a graph showing an example of the V(z) curve in the procedure for the analysis of the V(z) curve.
Figure 4B:
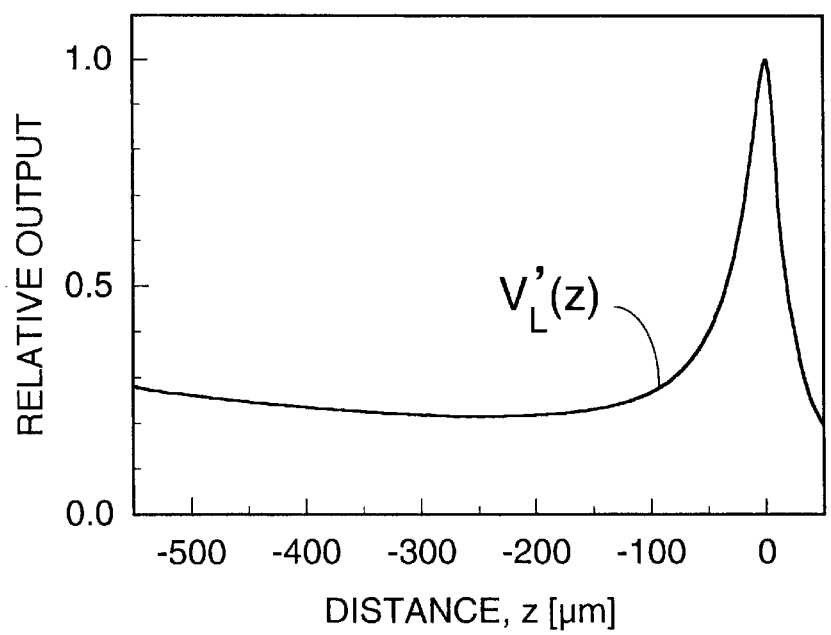
FIG. 4B is a graph showing a $V_L'(z)$ curve measured for Teflon, which is an approximation of the $V_L(z)$ curve.
Figure 5A:
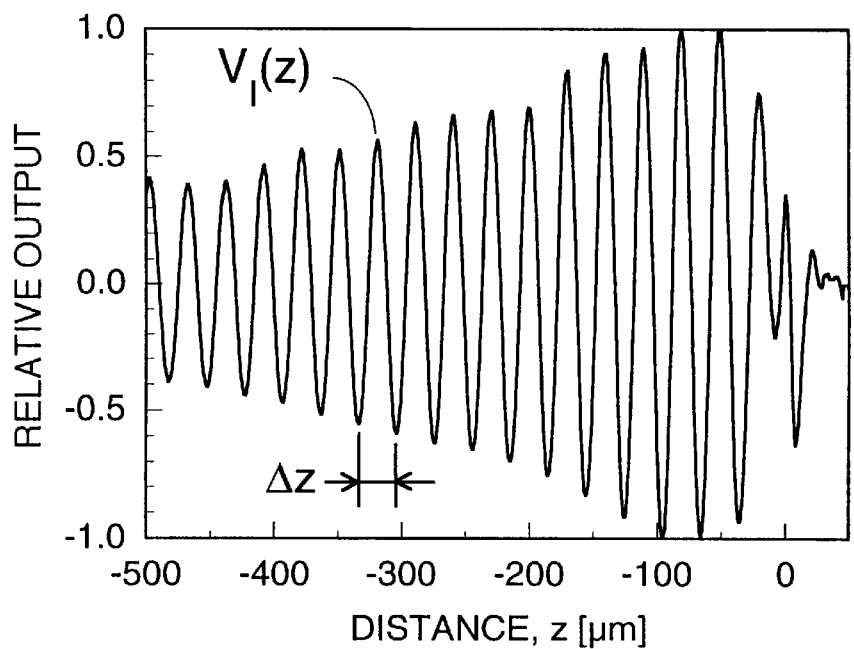
FIG. 5A is a graph showing a $V_I(z)$ curve.
Figure 5B:
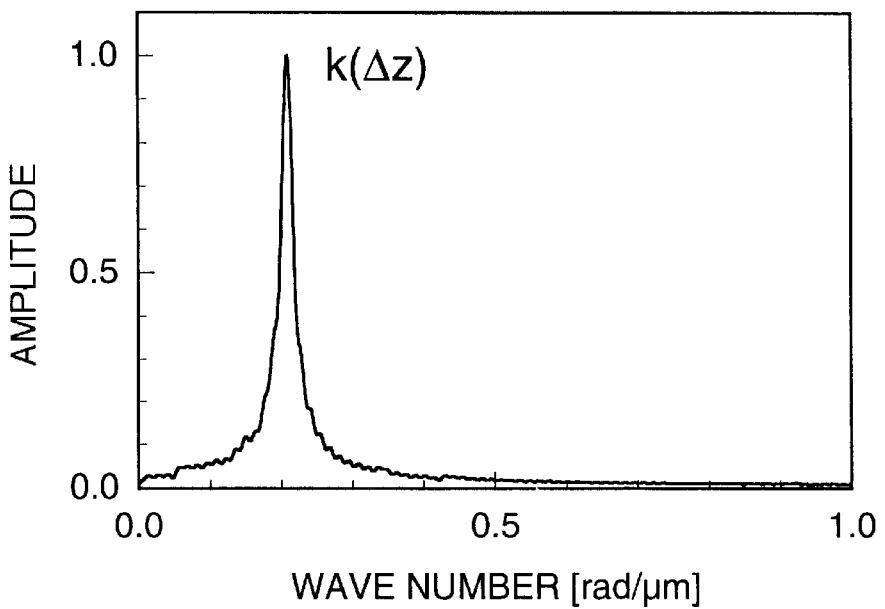
FIG. 5B is a graph showing a frequency spectrum distribution obtained by an FFT analysis of the $V_I(z)$ curve.
Figure 12A:
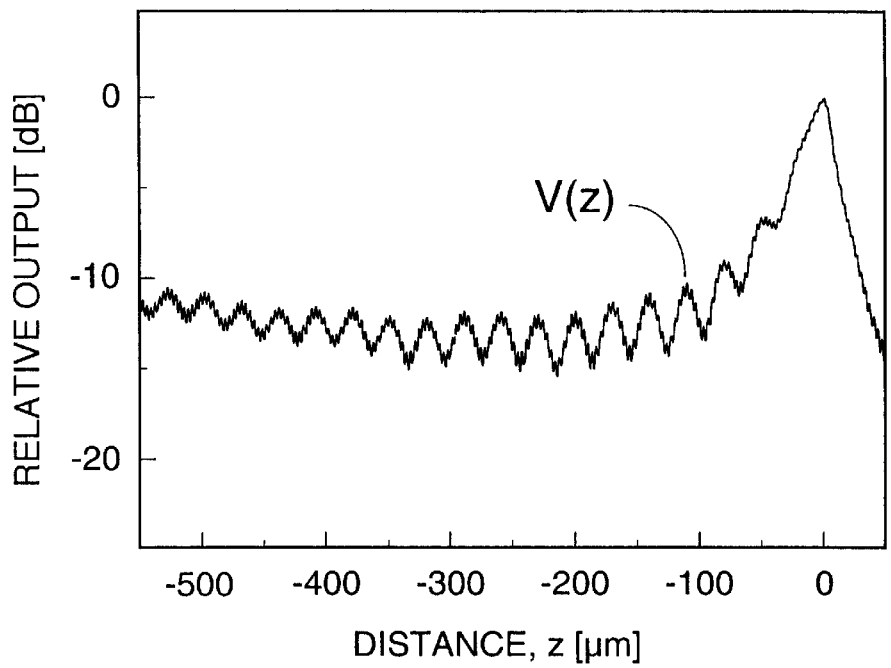
FIG. 12A is a graph showing an amplitude V(z) curve.

FIG. 12A depicts an example of the amplitude V(z) curve measured for the (111) GGG specimen (which is the same as shown FIG. 4) at the ultrasonic frequency f=225 MHz. The direction of the LSAW propagation is the same as in the case of FIG. 2. The ON/OFF ratio of the RF tone burst signal generator used is 75 dB, and the power values of the carrier signal of the RF tone burst signal for excitation of ultrasonic waves and the carrier leakage signal are +17 dBm and −58 dBm, respectively. At this time, the power values of the V(z) signal and the $V_e$ signal in the detected signal by the receiver 6B in FIG. 7 were −8 dBm and −38 dBm, respectively, in the case where the specimen was placed at the focal point (z=0) of the acoustic lens. A small interference waveform between the V(z) signal and $V_e$ signal is superimposed on the V(z) curve. Conventionally, the V(z) analysis removes the interference waveform by digital filtering as a spurious noise component or unnecessary component (see step S3 in FIG. 3), but the interference waveform can be used to determine the wave number $k_W$ as described below.

Figure 12B:
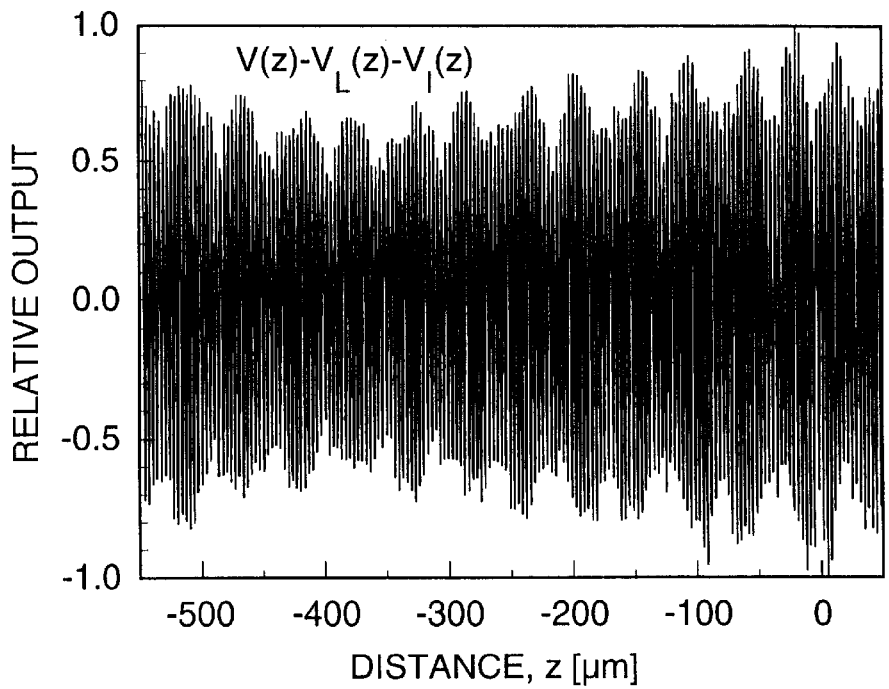
FIG. 12B is a graph showing interference components of a V(z) signal extracted by a moving average method after subtracting a characteristic curve of the ultrasonic device from the amplitude V(z) curve of FIG. 12A and a leakage electric signal.
Figure 13A:
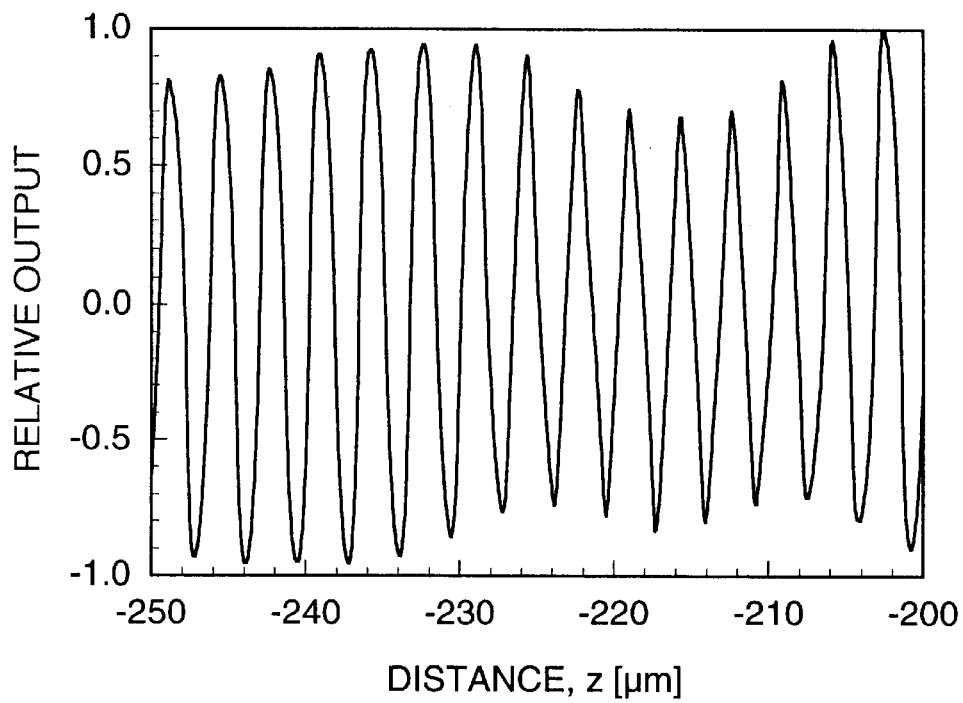
FIG. 13A is a graph showing, on an enlarged scale, the interference waveform in a region z=−250 μm to −200 μm in FIG. 12B.
Figure 13B:
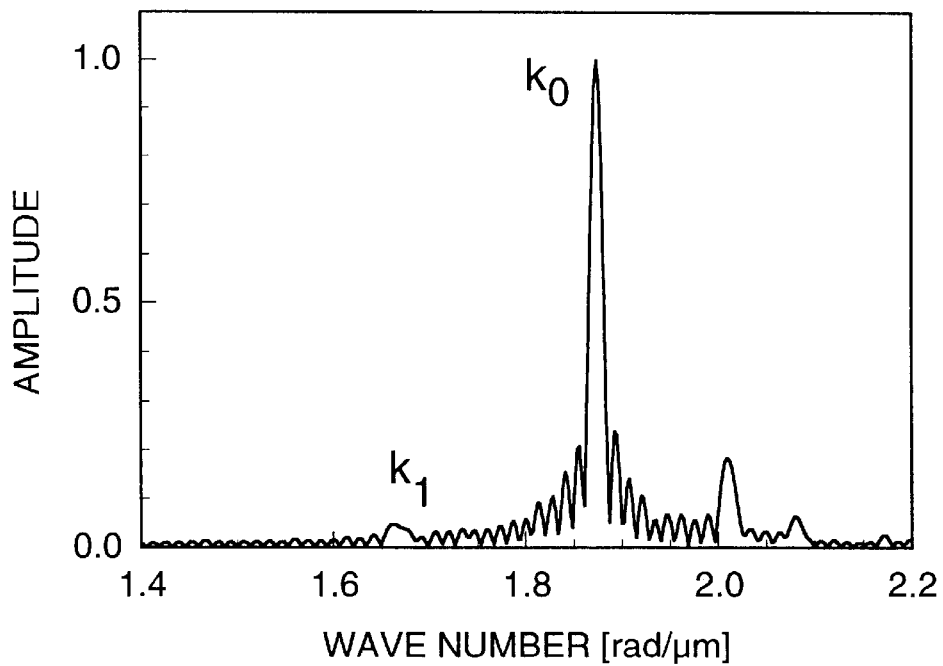
FIG. 13B is a graph showing a spectrum distribution obtained by an FFT analysis of the interference waveform in a region z=−500 μm to −30 μm in FIG. 12B.

FIG. 12B shows the interference component between the $V_e$ signal and the V(z) signal extracted by: subtracting the $V_L(z)$ curve, which is a characteristic curve of the ultrasonic device, from the V(z) curve shown in FIG. 12A; and removing the $V_I(z)$ curve through digital filtering. The $V_L(z)$ curve used in this example is a V(z) curve measured for a Teflon specimen in which no leaky surface acoustic waves are excited, and the digital filtering is the moving average method. FIG. 13A is a magnified view of the interference waveform in the range of z=−250 μm to −200 μm in FIG. 12B, from which it is seen that the waveform varies periodically. FIG. 13B depicts a frequency spectrum distribution obtained by an FFT analysis of the interference waveform in the range of z=−500 μm to −30 μm in FIG. 12B. The FFT analysis provides two spectra or peaks corresponding to $k_0(=2k_W)$ and $k_1(=2k_W \cos\theta_{LSAW})$, respectively. As is the case with the complex V(z) curve, the wave number $k_W$ is calculated from $k_W=k_0/2$.

When the ON/OFF ratio of the RF tone burst signal generator is sufficiently high, the amplitude of the $V_e$ signal is so small that the interference waveform (FIG. 12B) is difficult to observe. In such a case, however, a similar interference waveform can be obtained by an electrical interference method that uses, as a reference signal, a continuous wave signal provided from a signal generator for the carrier signal of the RF tone burst signal for the excitation of ultrasonic waves (see FIG. 19).

Figure 14:
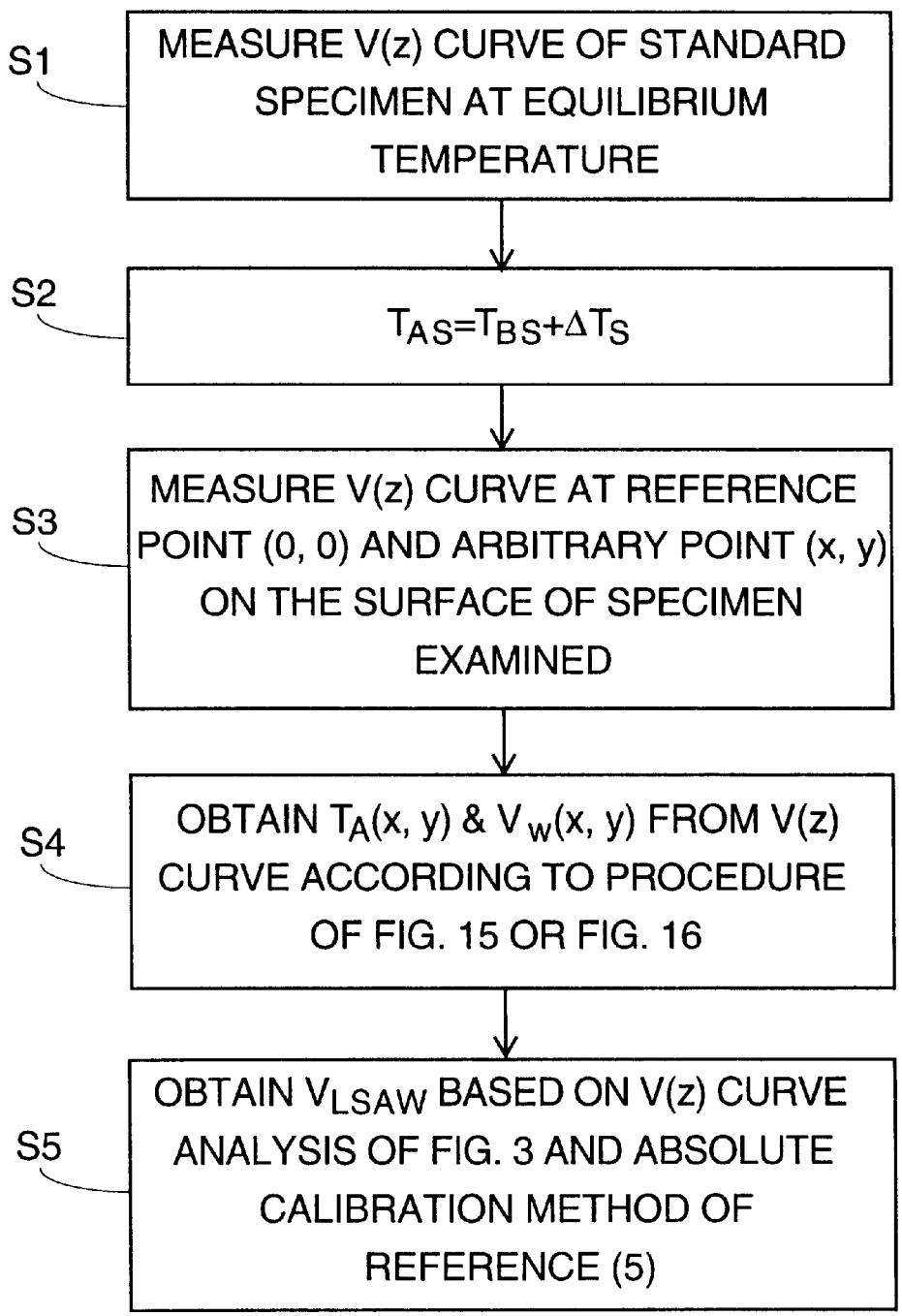
FIG. 14 is a flowchart showing a method for obtaining the LSAW velocity by removing temperature measurement errors in the measurement of the two-dimensional distribution of the LSAW velocity.
Figure 15:
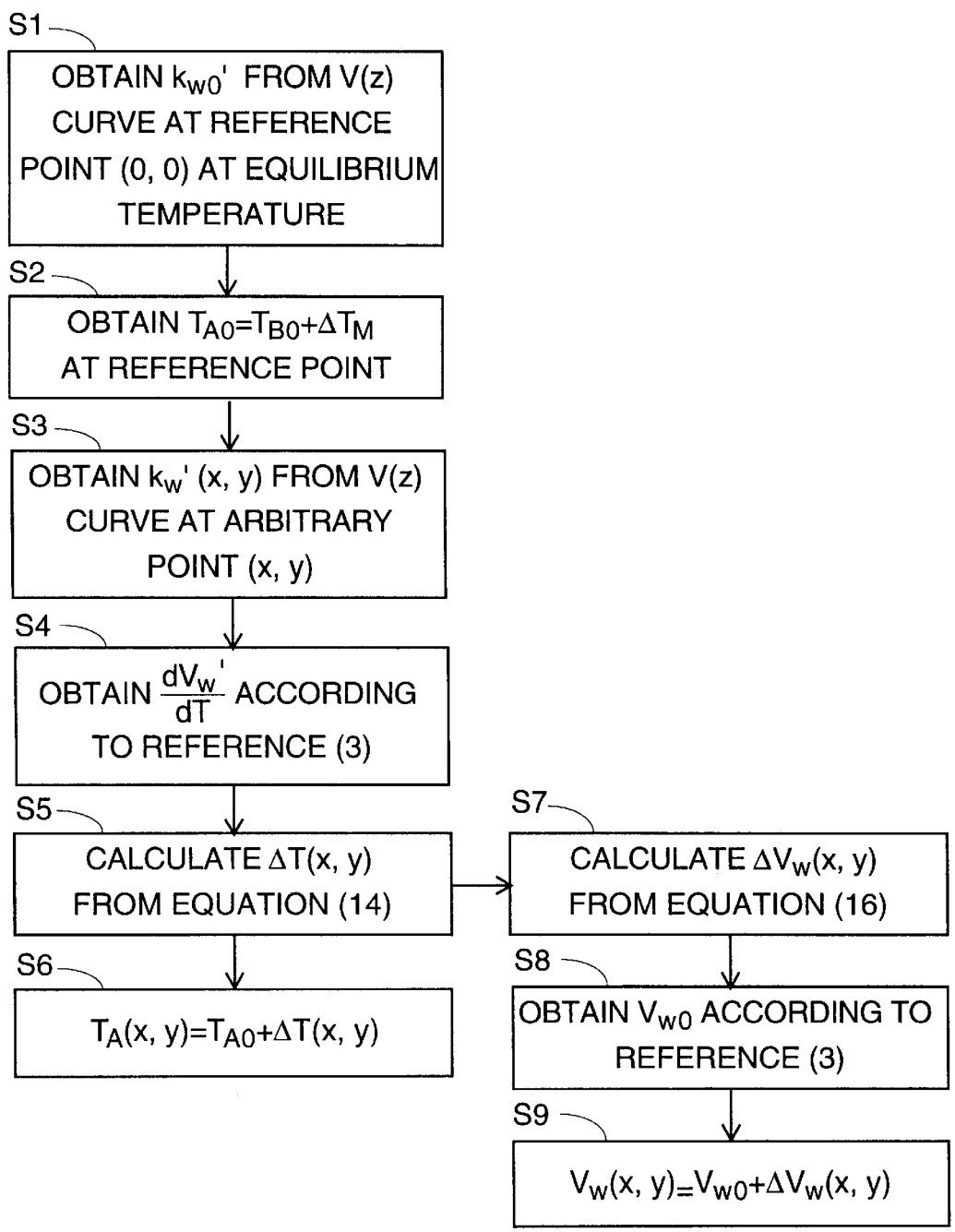
FIG. 15 is a flowchart of a method for obtaining the temperature and longitudinal wave velocity in an ultrasonic wave propagation region in the measurement of the two-dimensional distribution of the LSAW velocity from the wave number of a longitudinal wave obtained from the V(z) curve.
Figure 16:
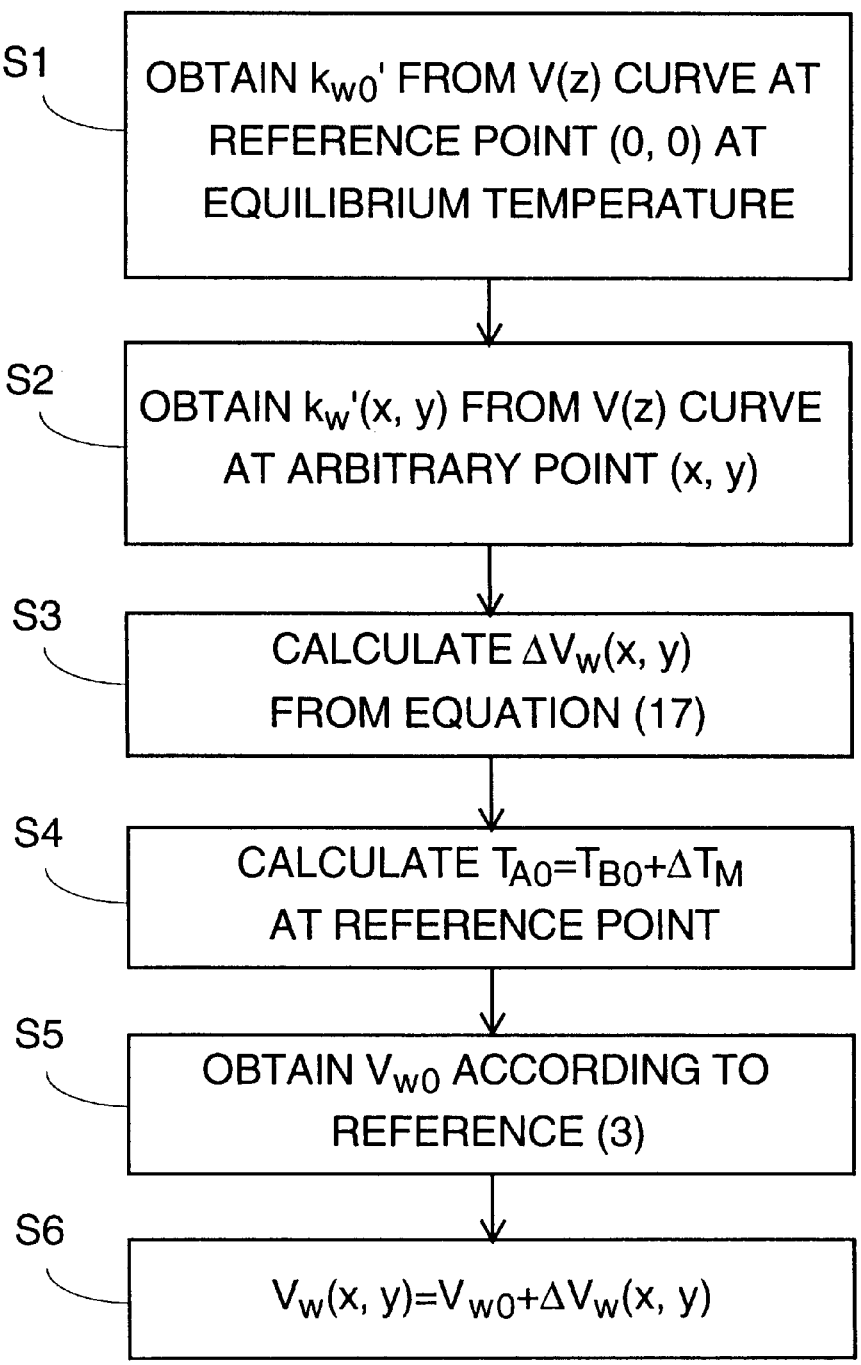
FIG. 16 is a flowchart of another method for obtaining the longitudinal wave velocity.

Incidentally, under the influences of its inherent frequency dependence given by Eq. (3) and the frequency characteristic caused by diffraction during propagation of ultrasonic waves, the wave number $k_W$ of the longitudinal wave derived from the V(z) curve slightly differs from the true wave number $k_W$ at the temperature $T_W$ and at the frequency f. The wave number is also influenced by the ultrasonic device used. Now, a description will be made of the procedure by which the temperature and the longitudinal wave velocity at an arbitrary point (x, y) in the ultrasonic wave propagation region in the water are determined, as the temperature $T_{A0}$ and longitudinal wave velocity $V_{W0}$ at the reference point (x, y)=(0, 0) under stable temperature conditions, from the wave number of the longitudinal waves derived from the V(z) curve to remove temperature measurement errors in the measurement of the two-dimensional LSAW velocity distribution and the LSAW velocity for the specimen under examination is determined. FIG. 14 depicts the procedure for measuring the two-dimensional $V_{LSAW}$ distribution, and FIGS. 15 and 16 depict the procedures for determining the temperature $T_A(x, y)$ and the longitudinal wave velocity $V_W(x, y)$ at the given point (x, y). The wave number of the longitudinal wave, which is derived from the V(z) curve, will hereinafter be identified by $k_W'$ in distinction from the true wave number $k_W$.

In FIG. 14 the procedure begins with measuring the V(z) curve for the standard specimen under stable temperature conditions (step 1). A temperature measurement value $T_{BS}$ in the region B at this time is compensated for by Eq. (9) with the temperature compensating parameter $\Delta T_S$ pre-measured for the standard specimen to obtain the temperature $T_{AS}$ in the ultrasonic wave propagation region (step S2). Next, the V(z) curve is measured at the reference point (0, 0) and the arbitrary point (x, y) on the surface of the specimen under examination (step 3), and the temperature $T_A(x, y)$ and longitudinal wave velocity $V_W(x, y)$ in the ultrasonic propagation region are obtained from the V(z) curve (step S4). After this, the velocity $V_{LSAW}$ is calculated by the V(z) curve analysis described previously with reference to FIG. 3 and the absolute calibration set forth in Reference (3).

While in the above the procedure has been described to start with measuring the V(z) curve for the standard specimen under stable temperature conditions and the temperature $T_{AS}$ (step S1 and S2 in FIG. 14), it is a matter of course that their measurements can be preceded by the measurement of the V(z) curve for the specimen under examination (steps S3 and S4 in FIG. 14). In the measurement of the V(z) curve at the fixed point, the stable or equilibrium state of the temperature $T_{A0}$ in the ultrasonic wave propagation region is decided by checking whether the longitudinal-wave wave number $k_{W0}'$ derived from the V(z) curve has become constant within a predetermined range.

FIG. 15 is a flowchart showing a concrete example of the procedure for calculating the longitudinal wave velocity $V_W(x, y)$ and the temperature $T_A(x, y)$ through utilization of the wave number obtained from the V(z) curve.

The water temperature $T_A(x, y)$ in the ultrasonic wave propagation region at the arbitrary point (x, y) during the measurement of the two-dimensional $V_{LSAW}$ distribution is expressed by the following equation (12) with reference to the temperature $T_{A0}$ at the reference point in the ultrasonic wave propagation region under stable temperature conditions.

$$T_A(x,y)=T_{A0}+\Delta T(x,y) \qquad (12)$$

In the first place, the wave number $k_W'$ is obtained by FFT analyzing the amplitude or complex V(z) curve measured at the reference point (x, y) under stable temperature conditions in step S3 in FIG. 14 (step S1). Then, the temperature $T_{A0}$ in the ultrasonic wave propagation region at this time is calculated by Eq. (9) using the temperature measurement value $T_{B0}$ in the vicinity of the ultrasonic beam and the precalculated temperature compensating parameter $\Delta T_M$ (step S2). The next step is to obtain the wave number $k_W'(x, y)$ from the V(z) curve measured at the arbitrary point on the specimen surface in step S3 in FIG. 14 (step S3).

Incidentally, in Eq. (12)

$$\Delta T(x, y) = \frac{V_W'(x, y) - V_{W0}'}{\frac{dV_W'}{dT}} \qquad (13)$$

where $V_W'$ bears a relationship of $V_W'=2\pi f/k_W'$ with $k_W'$ derived from the V(z) curve as indicated by Eq. (3). Hence, substitution of $\Delta T(x, y)$ and $k_W'$ into Eq. (13) gives $$\Delta T(x, y) = \frac{2\pi f\{k_{W0}' - k_W'(x, y)\}}{k_{W0}'k_W'(x, y)\frac{dV_W'}{dT}} \qquad (14)$$

It is considered that the rate of change of $V_W'$ to temperature, $dV_W'/dT$, is nearly equal to that of $V_W$. Accordingly, the rate of change is read out of a table that provides a list of rates of change corresponding to respective temperatures according to Reference (3) (step S4). Hence, $\Delta T(x, y)$ is given by Eq. (14) (step S5), and $T_A(x, y)$ is given by Eq. (12) (step S6).

Similarly, the longitudinal wave velocity $V_W(x, y)$ in the ultrasonic wave propagation region at the arbitrary point (x, y) during the measurement of the two-dimensional $V_{LSAW}$ distribution is expressed by the following equation (15) with reference to the longitudinal wave velocity $V_{W0}$ at the reference point in the ultrasonic wave propagation region under stable temperature conditions.

$$V_W(x,y) = V_{W0} + \Delta V_W(x,y) \tag{15}$$

where $\Delta V_W(x, y)$ is the amount of change in the longitudinal wave velocity with respect to the temperature change $\Delta T(x, y)$. The rate of change of the longitudinal wave velocity $V_W$ to temperature is 2.83 (m/s)/° C. at 23° C. (or so) according to Reference (3), and hence it is given by the following equation (16).

$$\Delta V_W(x, y) = \frac{dV_W}{dT} \cdot \Delta T(x, y) = 2.83 \cdot \Delta T(x, y) \tag{16}$$

Hence, when $\Delta T(x, y)$ is found, $\Delta V_W(x, y)$ is obtained (step S7), and $V_{W0}$ is obtained from $T_{A0}$ according to Reference (3) (step S8); therefore, $V_W(x, y)$ is given by Eq. (15) (step S9)

Alternatively, as depicted in FIG. 16, $k_{W0}'$ is obtained from the V(z) curve measured at the reference point (0, 0) under stable temperature conditions in step S3 in FIG. 14 (step S1), and $k_W'(x, y)$ is obtained from the V(z) curve measured at the arbitrary point (x, y) in step S3 in FIG. 14 (step S2). Since $\Delta V_W$ is given by the following equation (17) from Eq. (13) or Eq. (14), and Eq. (16), $\Delta V_W(x, y)$ is calculated from Eq. (17) in step S3.

$$\Delta V_W(x, y) = V_W'(x, y) - V_{W0}' = \frac{2\pi f \{k_{W0}' - k_W'(x, y)\}}{k_{W0}' k_W'(x, y)} \tag{17}$$

In step 4 the temperature $T_{A0}$ in the region A is derived from the measured temperature $T_{B0}$ in the region B, then in step S5 the ultrasonic wave velocity $V_{W0}$ in the water at the temperature $T_{A0}$ is calculated according to Reference (3), and in step S6 $V_W(x, y)$ is calculated by Eq. (15) from $V_{W0}$ and $\Delta V_W(x, y)$.

While in the above the measurement of $k_W'$ at the reference point (0, 0) on the surface of the specimen under examination under stable temperature conditions (step S1 in FIG. 15 and step S1 in FIG. 16) has been described to precede the measurement of $k_W'(x, y)$ at the arbitrary point (x, y) (step S3 in FIG. 15 and step S2 in FIG. 16), it is a matter of course that the former may be made halfway through or after the latter. Further, the reference point in the above is set at the origin (0, 0), but other points may be used as long as the temperature distribution has been measured.

Although the above procedure has been described in connection with the temperature of about 23° C., it is also applicable, of course, at other arbitrary temperatures.

Figure 7:
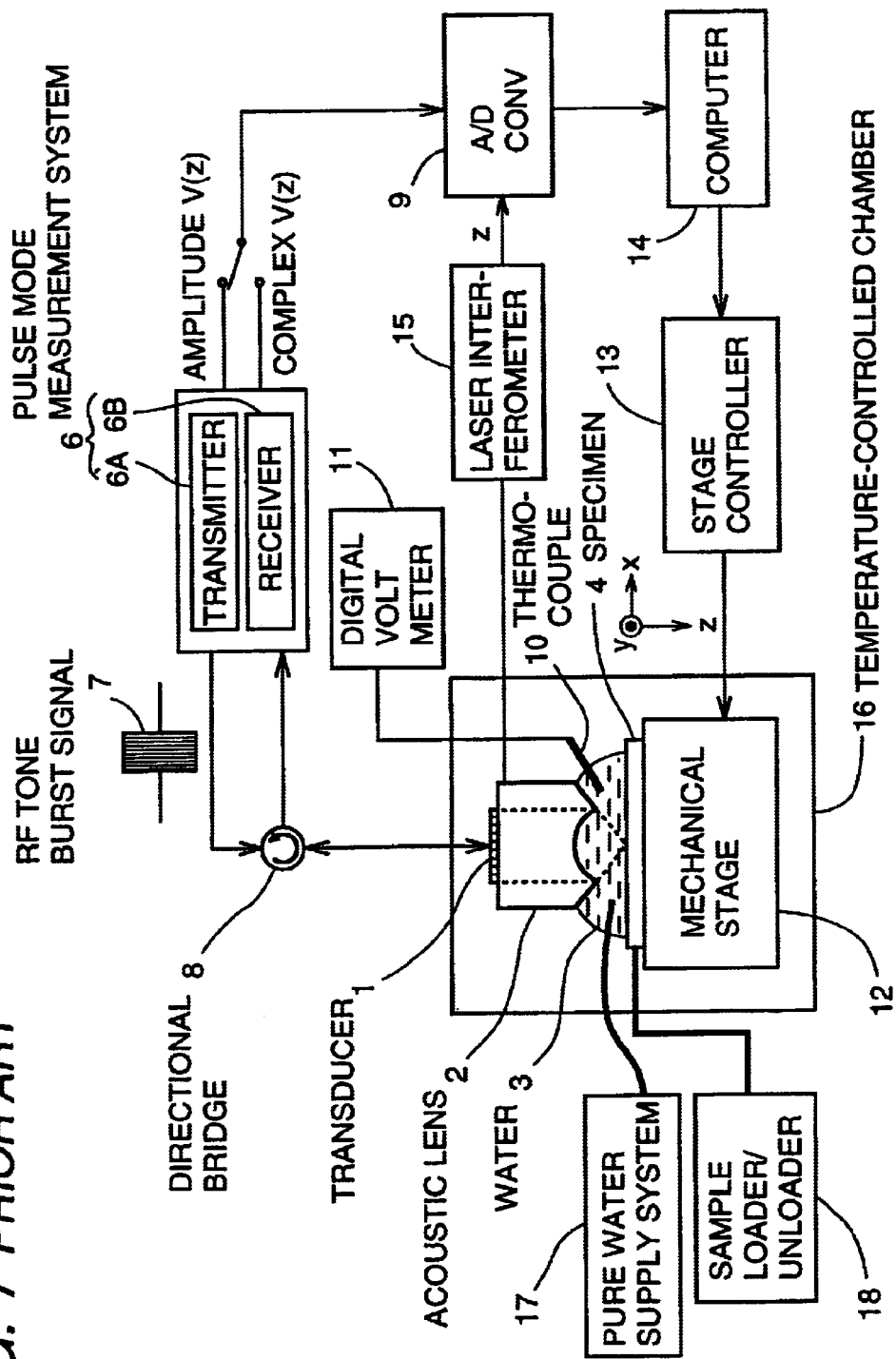
FIG. 7 is a block diagram of an LFB ultrasonic material characterization system.
Figure 17:
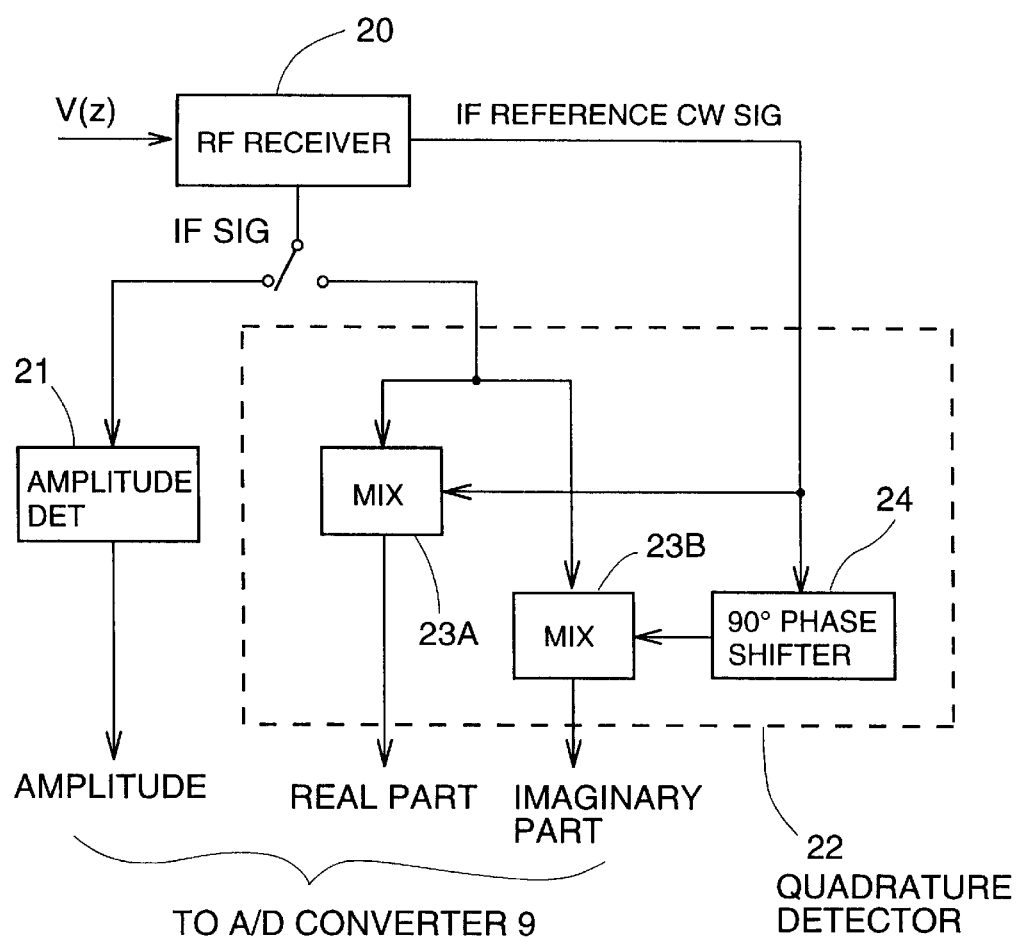
FIG. 17 is block diagram of a receiver for measuring the amplitude V(z) curve or the complex V(z) curve by a quadrature detection scheme.
Figure 18:
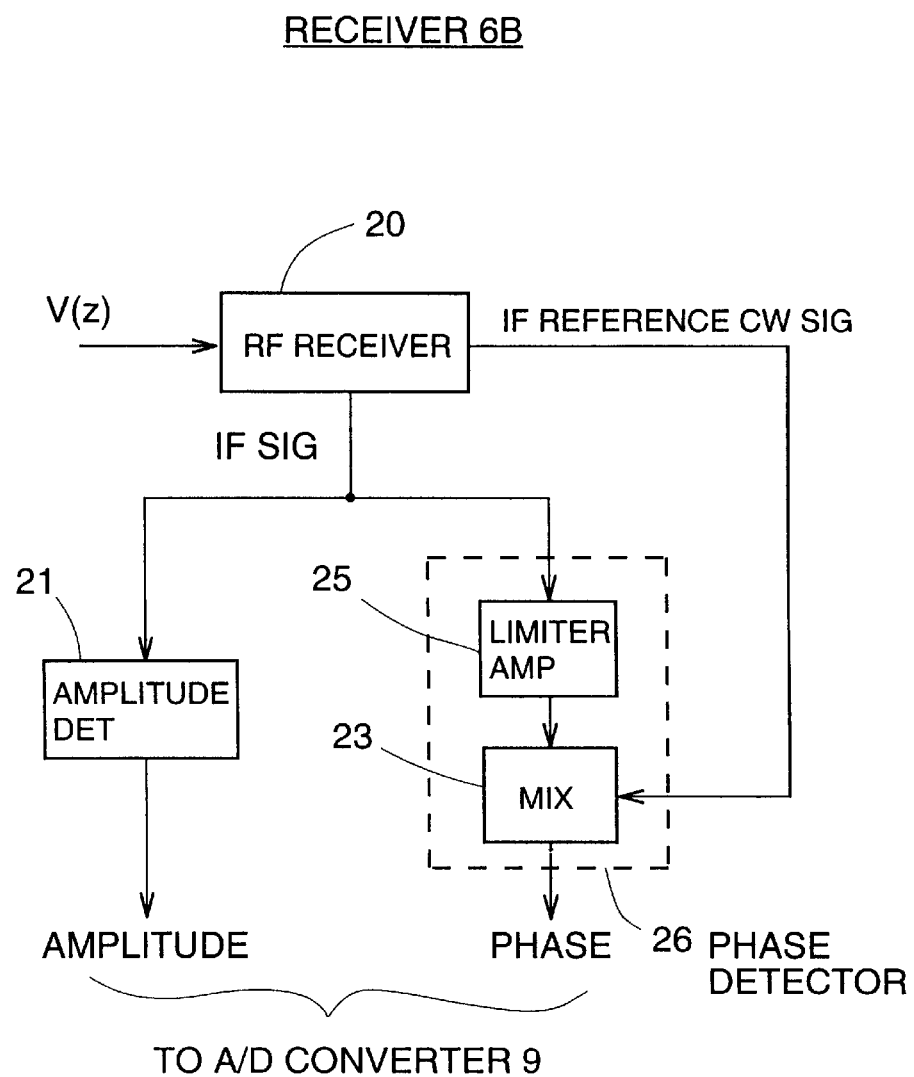
FIG. 18 is a block diagram of a receiver for measuring the amplitude and phase of the V(z) curve.
Figure 19:
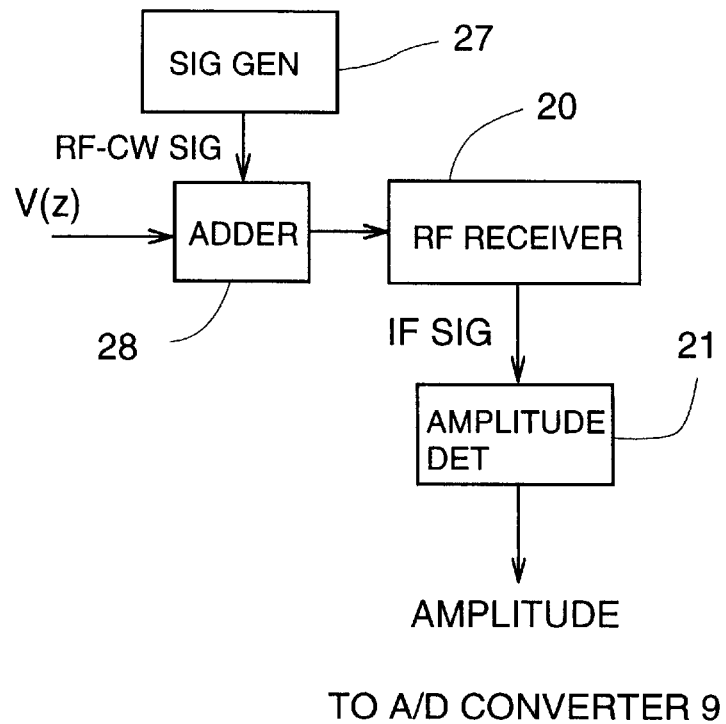
FIG. 19 is a block diagram depicting an example of an electric circuit for implementing electric interference to obtain an interference waveform of the V(z) signal and a continuous wave reference signal.

FIGS. 17, 18 and 19 illustrate in block form examples of the receiver 6B in the pulse mode measurement system 6 in FIG. 7 with which it is possible to measure the amplitude or complex V(z) curve. The receiver 6B of FIG. 17 is an example of a circuit for measuring the amplitude V(z) curve or the complex V(z) curve by quadrature detection. The V(z) signal fed to an RF receiver 20 is frequency-converted to an IF signal and its amplitude value is detected by an amplitude detector 21. Alternatively, in a quadrature detector 22 the real and imaginary parts of the complex V(z) curve are detected by mixers 23A and 23B and a 90° phase shifter 24 from the IF signal.

The receiver 6B of FIG. 18 is an example of a circuit for measuring the amplitude and phase of the V(z) signal. As is the case with the receiver of FIG. 17, the V(z) signal frequency-converted by the RF receiver 20 to the IF signal is amplitude-detected by the amplitude detector 21 and phase-detected by a phase detector composed of a limiter amplifier 25 and a mixer 23. The detected phase information can also be used to obtain $k_W'$.

The receiver 6B of FIG. 19 illustrates an example of a circuit for performing an electrical interference method to generate a waveform of interference between the V(z) signal and a continuous wave reference signal which is used to obtain the V(z) curve and $k_W'$ in the measurement of the amplitude V(z) curve. An RF-CW reference signal from an RF signal generator 27 is added by an adder 28 to the V(z) signal, and the adder output is converted by the RF receiver 20 to an IF signal, whose amplitude is detected by the amplitude detector 21.

In the receivers 6B of FIGS. 17 and 18 the V(z) signal is detected after being frequency converted, but of course, the it may also be detected as the RF signal by the RF-CW reference signal. In the receiver of FIG. 19, too, the V(z) signal may be amplitude detected after being frequency converted to the IF signal and added with the IF-CW reference signal.

EMBODIMENT

A description will be given first of an example in which the water temperature distribution was measured by thermocouples at one fixed point on the specimen surface centrally thereof. In a 200-MHz-band LFB ultrasonic device with a 1-mm radius of lens curvature, temperature was measured by thermocouples in the regions A and B depicted in FIG. 8 to check the temperature difference between the regions A and B. The thermocouples were spaced about 3 mm apart, and in the region A the distance between the cylindrical surface of the acoustic lens and the specimen was set equal to the focal length (1.15 mm) of the acoustic lens. The XY stage is set at the origin (x=y=0). The thermocouples are each absolutely calibrated by ±0.01° C., and the relative error between the both thermocouples is within ±0.005° C. The entire mechanical stage, including the specimen, is placed in a temperature-controlled chamber, in which the relative humidity is 40±1%.

Now, consider the thermal conduction system [air/water-couplant/specimen/specimen-holder]. When water is supplied to the specimen held in temperature equilibrium in the temperature-controlled chamber, the specimen temperature drops due to the heat of vaporization of the water, developing a temperature gradient in the above-mentioned thermal conduction system. It is considered that the temperature gradient depends on the quantity of water, the thermal conductivity of the specimen and its thickness.

Figure 6:
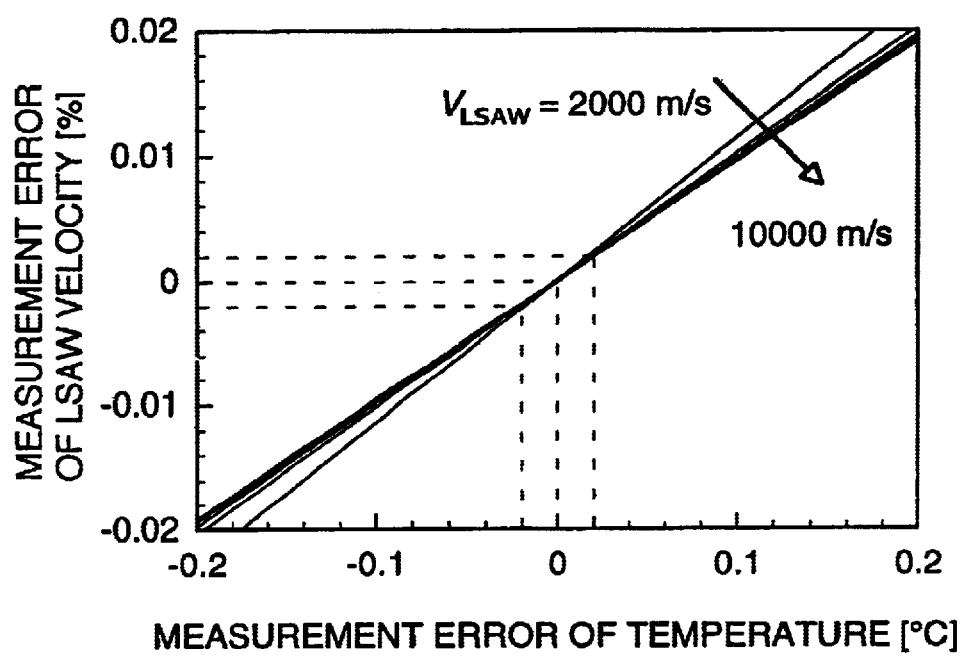
FIG. 6 is a graph showing numerically calculated values of LSAW velocity measurement errors with respect to water temperature measurement errors.
Figure 20A:
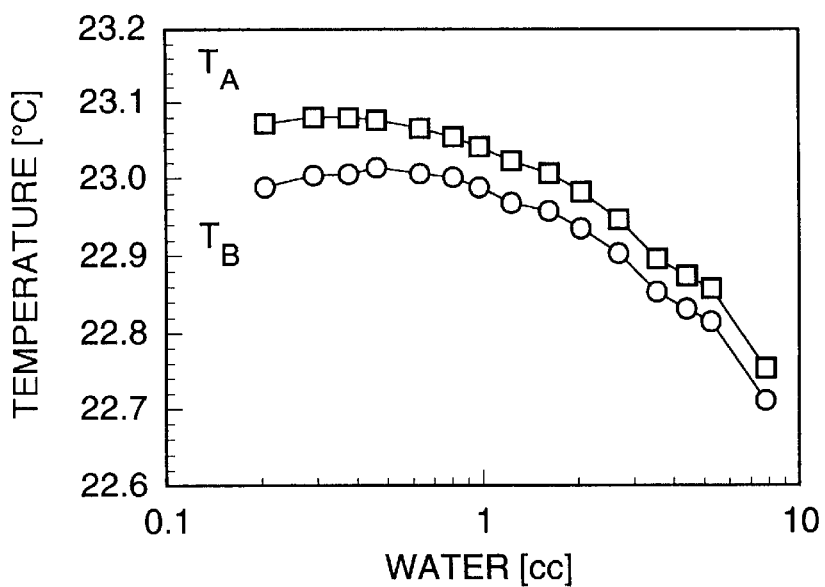
FIG. 20A is a graph showing measurement values of the relationships between the water temperatures in regions A and B and the quantity of water in FIG. 8.
Figure 20B:
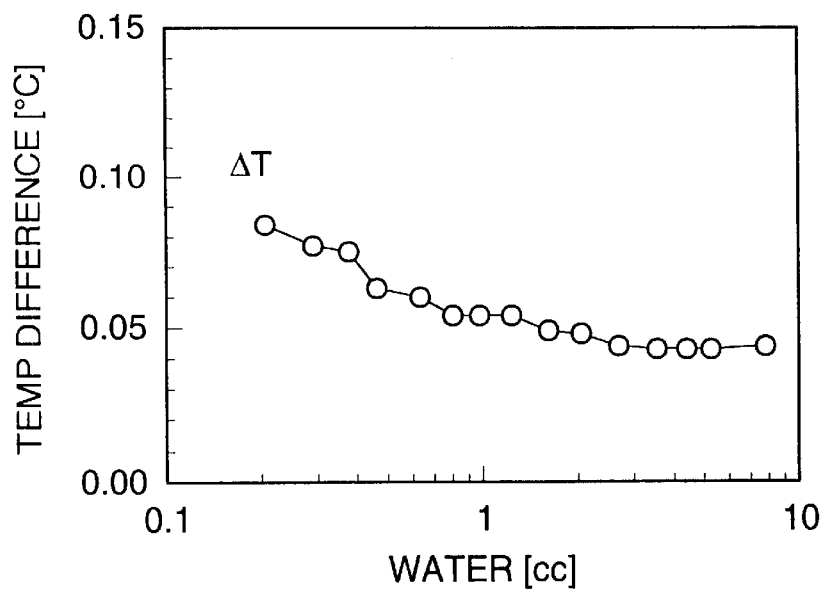
FIG. 20B is a graph showing the relationship of the temperature difference between the regions A and B to the quantity of water.

In the first place, a study is made of the relationship between the quantity of water and the temperature distribution. A (111) GGG specimen was held on the specimen holder suction and the measurement was conducted when the water temperature became sufficiently stable after supplying the water. The measurement values are shown in FIG. 20A. The temperature $T_B$ (indicated by O) in the region B in the vicinity of the lens surface is lower than the temperature $T_A$ (indicated by □) in the region A directly below the lens surface because of the heat of evaporation of the water. The temperatures $T_A$ and $T_B$ both drop with an increase in the quantity of water. The reason for this is considered that an increase in the quantity of water increases the surface area of water contacting the air to increase the amount of water evaporated accordingly and hence lose much heat of evaporation. FIG. 20B shows the temperature difference $T_A - T_B$ between the two measuring points calculated by Eq. (8), that is, the temperature compensating parameter $\Delta T$. It is seen that the temperature difference $\Delta T$ increases with a decrease in the amount of water. In the apparatus used, when the quantity of water is 0.5 cc or more, ΔT is within 0.053±0.01° C., corresponding to the measurement error within −0.0053±0.001% from FIG. 6. When the quantity of water is in the range from 0.6 cc to 1.2 cc, the temperature difference ΔT is as small as 0.057±0.003° C. At this time, the LSAW velocity measurement error is within −0.0057±0.0003% as seen from FIG. 6. Assuming, for example, that the initial quantity of water is 1.2 cc, even if the measurement is carried out for a long time (two to three hours, for instance) and the quantity of water is somewhat decreased by evaporation, variations in the temperature difference are small as long as the amount of water remaining is 0.5 cc or more.

Figure 21A:
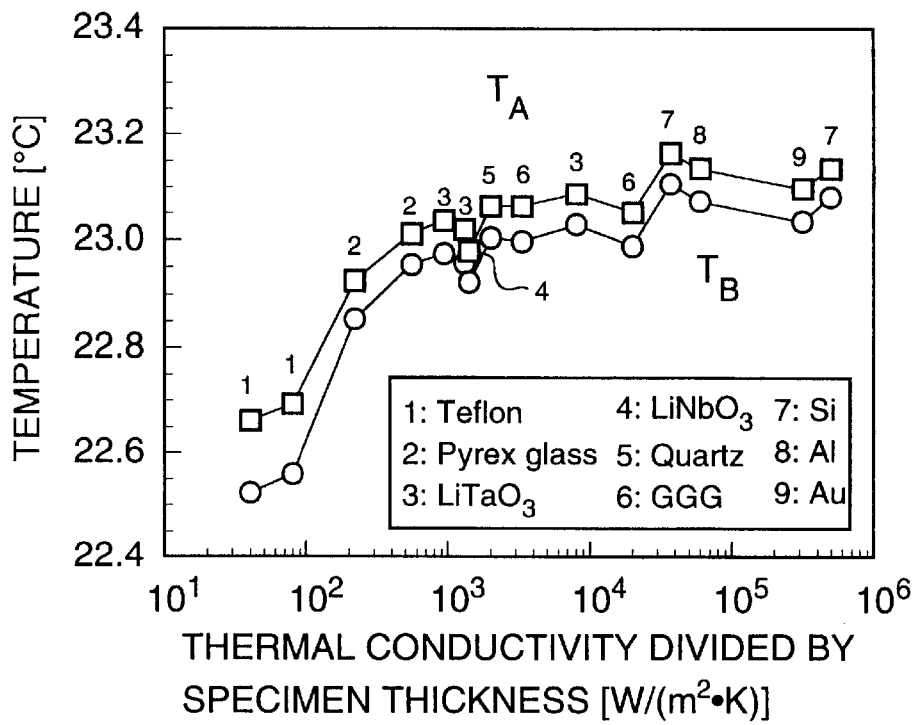
FIG. 21A is a graph showing measurement values of the relationships between the water temperatures in the regions A and B and the thermal conductivity of the specimen in FIG. 8.
Figure 21B:
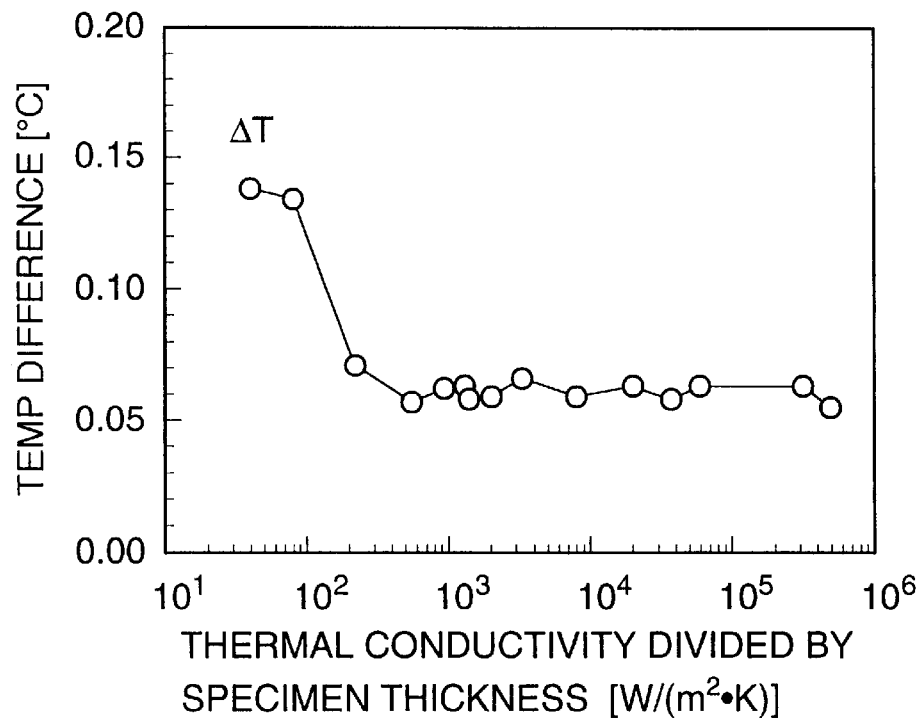
FIG. 21B is a graph showing the relationship of the temperature difference between the regions A and B to the thermal conductivity of the specimen.

Next, in order to study the relationships between the thermal conductivities and thicknesses of specimens and the temperature distribution in the water, temperatures in the regions A and B were measured using various solid specimens. The quantity of water used is 0.7 cc. The measurement values are shown in FIG. 21A. The abscissa represents the value obtained by dividing the thermal conductivity of the specimen by its thickness. The temperature in the region A immediately below the lens surface ($T_A$ indicated by □) is higher than the temperature in the region B. It is seen that under the measurement conditions used, the water temperature differs with the thermal conductivity of each specimen and rises with an increase in the thermal conductivity. FIG. 21B shows the temperature difference ΔT between the two measuring points calculated by Eq. (8) with respect to the measurement values shown in FIG. 21A. It is seen that the temperature difference also depends on the thermal conductivity. The temperature difference ΔT increases with a decrease in the thermal conductivity; under the measurement conditions used, the temperature difference varies in the range of 0.05 to 0.14° C. According to our experiments, in single-crystal, glass and metal specimens whose material properties are often evaluated by the LFB ultrasonic material characterization system and whose thermal conductivities divided by their thicknesses are in the range of $2 \times 10^2$ to $5 \times 10^5$ W/(m$^2$·K), the temperature difference is in the range of 0.063±0.008° C. as long as the quantity of water used for every specimen is 0.7 cc. This temperature measurement error corresponds to −0.0063±0.0008% in terms of the LSAW velocity measurement error according to FIG. 6.

As described above, the measurement of the V(z) curve at one fixed point on the specimen surface centrally thereof under the above-mentioned measurement conditions is started after the water temperature distribution becomes stable, and the water temperature measurement values by the thermocouples are compensated for by the temperature compensating parameter ΔT pre-measured for each specimen, whereby the temperature in the ultrasonic wave propagation region can be obtained with high accuracy. For the specimens whose thermal conductivities divided by their thicknesses are in excess of $2 \times 10^2$ W/(m$^2$·K), if the measurement conditions such as the quantity of water are common, the LSAW velocity measurement errors due to the water temperature distribution can be removed by the absolute calibration using the standard specimen without compensating for the water temperature measurement values by ΔT. It can be said that when the quantity of water is held constant, the LSAW velocity measurement error caused by the water temperature distribution is within ±0.0008%, and that when the quantity of water is in the range of 0.6 to 1.2 cc, the LSAW velocity measurement error is within ±0.0011% including the error ±0.0003% corresponding to a temperature difference variation ±0.003° C. resulting from a change in the quantity of water. That is, the procedure of FIG. 9 permits highly accurate measurement of the LSAW velocity. When the distance between the acoustic lens surface and the specimen was 1.75 mm, too, about the same results as mentioned above were obtained.

Next, a description will be given of an example in which: the longitudinal-wave wave number $k_W'$ in the ultrasonic propagation region in the water is derived from the V(z) curve measured under the measurement conditions where the temperature difference in the water may change as in the case of the measurement of the two-dimensional LSAW velocity distribution; variations in temperature and in the longitudinal wave velocity are estimated by the procedure shown in FIG. 15 or 16; and the LSAW measurement error is corrected by the procedure of FIG. 14. The specimen used is a 36°-rotated Y-cut lithium tantalate (LiTaO$_3$) single-crystal substrate of a 3 in. diameter. The direction of LSAW propagation is the crystallographic X-axis direction, and the ultrasonic frequency f is 225 MHz. The quantity of water is 0.7 cc.

A description will be given first of an example of correcting the LSAW distribution measurement value by the measurement and analysis of the complex V(z) curve. In the first place, with a view to obtaining the reference temperature $T_{A0}$, the complex V(z) curve was measured 50 times at the center (x=y=0) of the specimen surface after the water temperature became sufficiently stable. The average value of the water temperature measurement values by the thermocouple was $T_{B0}$=22.894° C. The temperature compensating parameter at this time is $\Delta T_M$=0.063° C. from the value for the lithium tantalate single crystal (3: LiTaO$_3$) shown in FIG. 21B. Hence, $T_{A0}$=22.957° C. from Eq. (9).

Figure 22A:
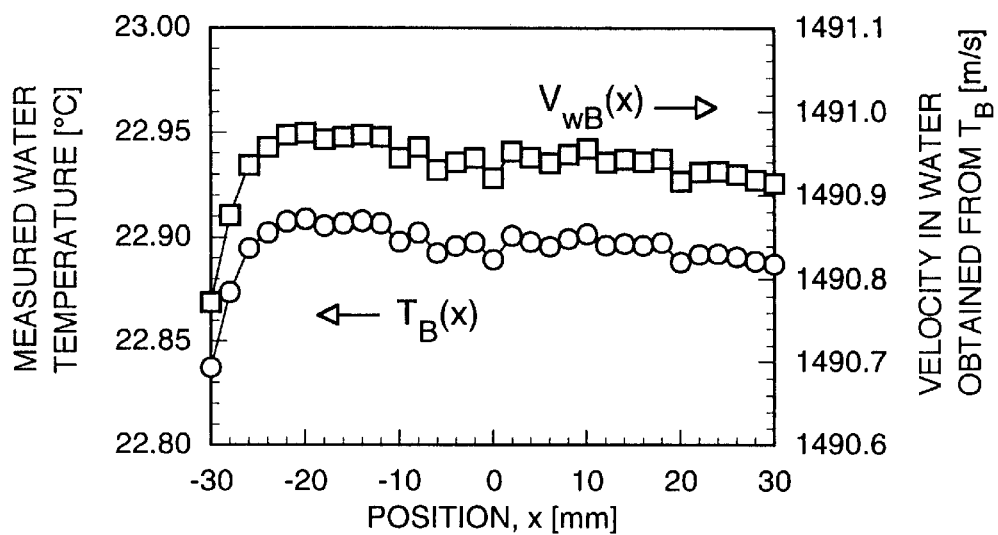
FIG. 22A is a graph showing the water temperature $T_B(x)$ measured by a thermocouple during the complex V(z) curve measurement and the longitudinal wave velocity $V_{WB}(x)$ in the water calculated from the water temperature $T_B(x)$.

FIG. 22A shows the LSAW velocity distribution obtained by translating the X stage in 2 mm steps over a distance of ±30 mm on the specimen surface and, at the same time, measuring the complex V(z) curve at each position x. In the following description, the y-coordinate notation will be omitted since y=0 at all times. Indicated by O in FIG. 22A is the water temperature measurement value $T_B(x)$ by the thermocouple during the V(z) curve measurement. The temperature was measured in the region B shown in FIG. 8. The temperature measurement value varies a maximum of 0.071° C. as the X stage is translated. The temperature sharply drops, in particular, at x<−24 mm. It is considered that this is because of a substantial change in the temperature environment around the water couplant near the edge of the specimen on the side thereof where the thermocouple is placed. Indicated by □ in FIG. 22A is the longitudinal wave velocity $V_{WB}(x)$ derived from the measured value $T_B(x)$ at each position x according to Reference (3). As a matter of fact, $V_{WB}(x)$ sharply drops at x<−24 mm as is the case with the water temperature. The LSAW velocity was calculated by Eq. (7) using the longitudinal wave velocity $V_{WB}(z)$ without temperature correction, and subjected to absolute calibration with a GGG standard specimen by the conventional procedure; the calibrated value is plotted by the O in FIG. 23B. Only the amplitude value is used in the V(z) curve analysis. The LSAW velocity varies a maximum of 0.287 m/s, and substantially decreases particularly at x<−24 mm.

Figure 22B:
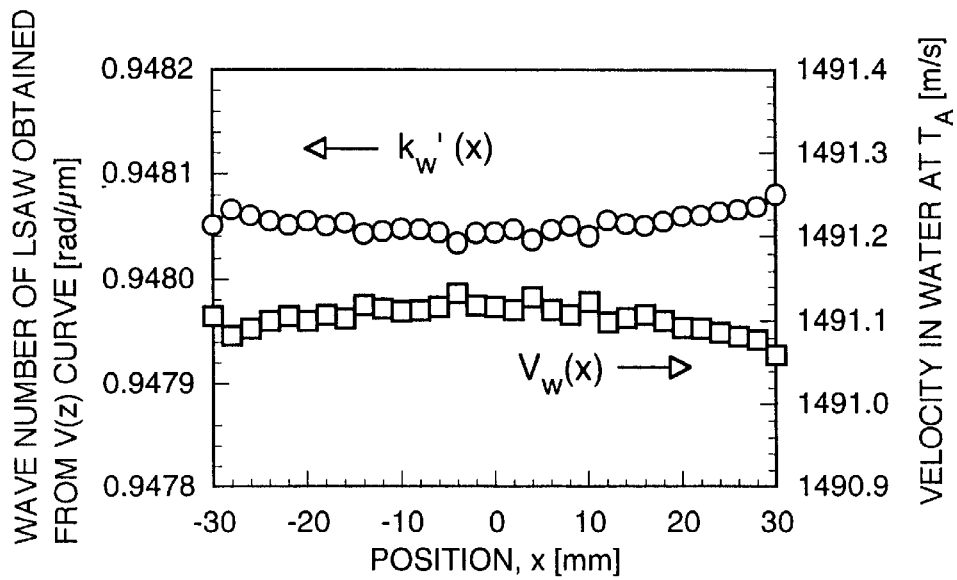
FIG. 22B is a graph showing $k_W'(x)$ obtained from the complex V(z) curve and $V_W(x)$ in the ultrasonic wave propagation region.

The wave number $k_W'(x)$ obtained from the measured complex V(z) curve is indicated by O circles in FIG. 22B. The temperature difference ΔT(x) from the reference temperature $T_{A0}$ at each position x, calculated by Eq. (14) from $k_W'$ is indicated by O in FIG. 23A. Further, $T_A(x)$ calculated by Eq. (12) from ΔT(x) is indicated by □. The average value of $T_A(x)$ is 22.947° C., and its maximum variation is 0.026° C. It can be seen that $T_A(x)$ varies less than $T_B(x)$ (which varies a maximum of 0.071° C.) indicated by O in FIG. 22A. This suggests that the temperature directly below the surface of the acoustic lens (the region A in FIG. 8) does not change as in the region where the temperature is monitored by the thermocouple (the region B in FIG. 8). For reference, an estimate of the temperature difference between the two regions from $T_A(x)$ and $T_B(x)$ is a maximum of 0.111° C. at x=−30 mm and a minimum of 0.038° C. at x=−20 mm. This indicates that in the measurement of the two-dimensional LSAW velocity distribution the temperature difference between the ultrasonic wave propagation region and the temperature monitoring region varies between 0.038 and 0.111° C. according to the position x, and that the measurement of the two-dimensional LSAW velocity distribution calls for taking into account the influence of the temperature difference at each position x. Indicated by □ in FIG. 22B is the longitudinal wave velocity $V_W(x)$ calculated by Eqs. (15) and (16) (or Eqs. (15) and (17)). This $V_W(x)$ is flatter than the velocity $V_{WB}(x)$ derived from the temperature measurement value (indicated by □ in FIG. 22A). Further, no drop is seen at x<−24 mm.

The LSAW velocity was calculated by Eq. (7) using $V_W(x)$ indicated by □ in FIG. 22B, and subjected to absolute calibration (see Reference (5)) with a (111) GGG standard specimen; the calibrated value is indicated by □ in FIG. 23B. Incidentally, the temperature measurement value $T_{BS}$ in the complex V(z) curve measurement for the standard specimen was corrected by the temperature compensating parameter $\Delta T_S=0.066°$ C. for the (111) GGG standard specimen shown in FIG. 21B (6 at the left handside: GGG). As a result, the true LSAW velocity distribution could be obtained; the maximum deviation of the LSAW velocity is 0.176 m/s and ±2σ (where σ is a standard deviation) is ±0.0029%. That is, it can be said that a decrease in the LSAW velocity at x<−24 mm is not caused by a change in the acoustic characteristic of the specimen but is a measurement error by a change in the water temperature distribution.

Next, a description will be given of an example of correcting the LSAW velocity distribution measurement value by the measurement and analysis of the amplitude V(z) curve. As is the case with the complex V(z) curve described above, the amplitude V(z) curve was measured 50 times at the center (x=y=0) of the specimen surface under water temperature stable conditions, by which a reference temperature $T_{A0}=22.957°$ C. was obtained.

Figure 24A:
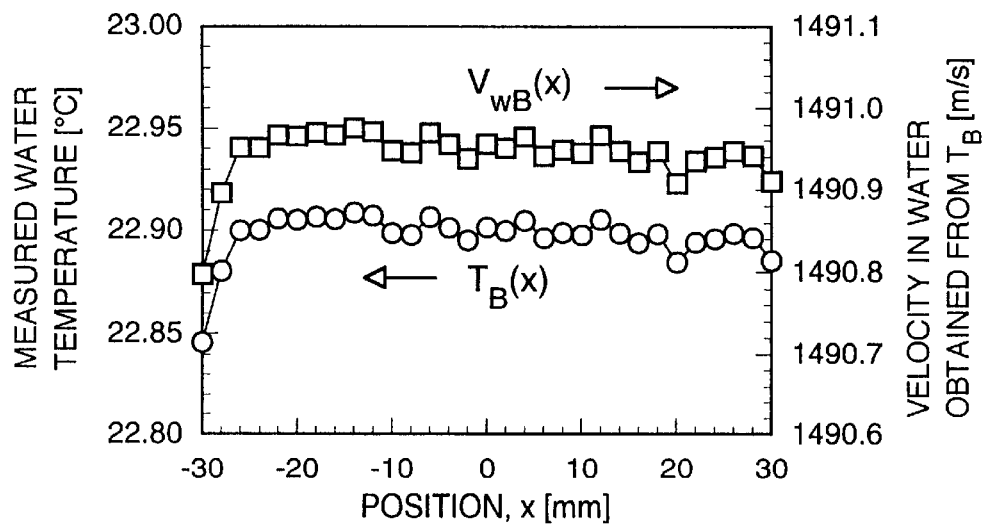
FIG. 24A is a graph showing the water temperature $T_B(x)$ measured by the thermocouple during the amplitude V(z) curve measurement and the longitudinal wave velocity $V_{WB}(x)$ in the water calculated from $T_B(x)$.

Following this, the LSAW velocity distribution was investigated by translating the X stage in 2 mm steps over a distance of ±30 mm on the specimen surface and, at the same time, measuring the complex V(z) curve at each position x. In FIG. 24A, O indicates the water temperature $T_B(x)$ measured by the thermocouple during the V(z) curve measurement. The temperature measurement value varies a maximum of 0.063° C. as the X stage is translated. The temperature sharply drops, in particular, at points x<−24 mm. In FIG. 24A, □ indicates the longitudinal wave velocity $V_{WB}(x)$ derived from the measured value $T_B(x)$ according to Reference (3). The LSAW velocity was calculated by Eq. (7) using the longitudinal wave velocity $V_{WB}(z)$ without temperature correction by the conventional procedure, and subjected to absolute calibration with a GGG standard specimen; the calibrated value is indicated by O in FIG. 25B. The LSAW velocity varies a maximum of 0.260 m/s.

Figure 24B:
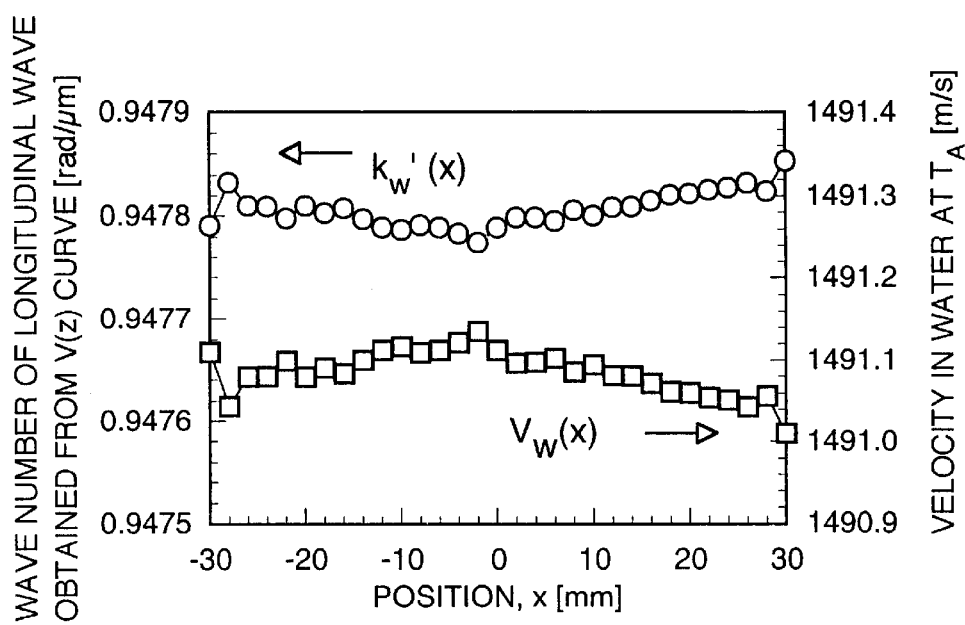
FIG. 24B is a graph showing $k_W'(x)$ obtained from the amplitude V(z) curve and $V_W(x)$ in the ultrasonic wave propagation region.

In FIG. 24B, $k_W'(x)$ obtained from the measured amplitude V(z) curve is indicated by O in FIG. 24B. The temperature difference $\Delta T(x)$ from the reference temperature $T_{A0}$ at each position x, calculated from $k_W'(x)$, is indicated by O in FIG. 25A. Further, $T_A(x)$ calculated from $\Delta T(x)$ is indicated by □ in FIG. 25A. The average value of $T_A(x)$ is 22.947° C., and its maximum variation is 0.044° C. For reference, an estimate of the temperature difference between the temperature measurement region and the ultrasonic wave propagation region, calculated from $T_A(x)$ and $T_B(x)$, is a maximum of 0.110° C. at x=−30 mm and a minimum of 0.034° C. at x=26 mm. The longitudinal wave velocity $V_W(x)$ calculated by Eqs. (15) and (16) (or Eqs. (15) and (17)) from $\Delta T(x)$ is indicated by □ in FIG. 24B.

The LSAW velocity was calculated by Eq. (7) using $V_W(x)$ indicated by □ in FIG. 24B, and subjected to absolute calibration with a (111) GGG standard specimen; the calibrated value is indicated by □ in FIG. 25B. Incidentally, the temperature measurement value $T_{BS}$ in the amplitude V(z) curve measurement for the GGG standard specimen was corrected by the temperature compensating parameter ($\Delta T_S=0.066°$ C.). The maximum deviation of the LSAW velocity is 0.177 m/s and ±2σ (where σ is a standard deviation) is ±0.0029%. In this case, too, about the same results as in the case of using the complex V(z) curve could be obtained.

In the above, the temperature difference $\Delta T$ for various specimens is used as the temperature compensating parameter, but even if an average $\Delta T$ value 0.061° C. for specimens whose thermal conductivities divided by their ticknesses (shown in FIG. 21B) are in the range of $2 \times 10^2$ to $5 \times 10^5$ W/(m²·K) is used, the temperature difference for each specimen is within 0.005° C.—this is within 0.0005% in terms of an LSAW velocity measurement error. While the present invention has been described as being applied to the measurement of the two-dimensional LSAW velocity distribution in the x-axis direction, the invention is applicable equally as well to the measurement in the y-axis direction or in both x- and y-axis directions.

Figure 23A:
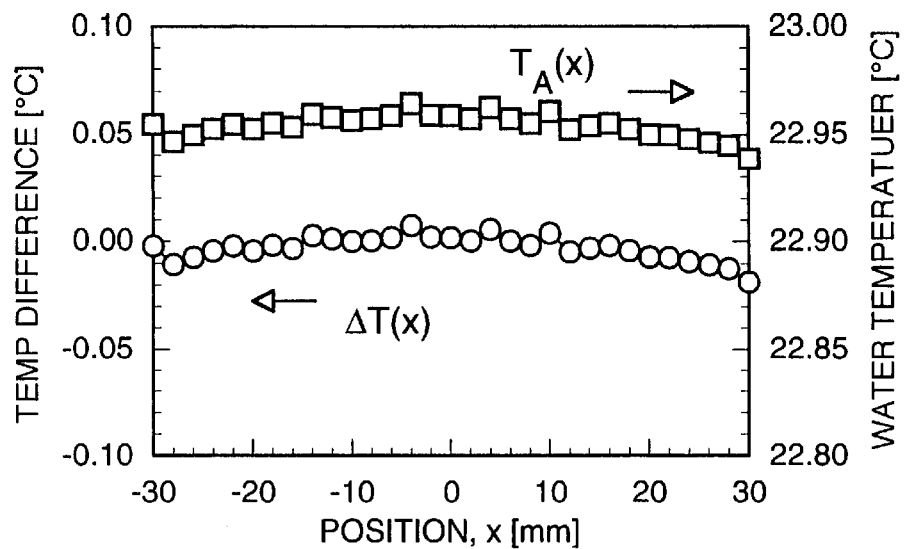
FIG. 23A is a graph showing a temperature difference $\Delta T(x)$ from a reference temperature $T_{A0}$ at each position x, calculated from $k_W'(x)$ in FIG. 22B, and $T_A(x)$ in the ultrasonic wave propagation region calculated from $\Delta T(x)$.
Figure 23B:
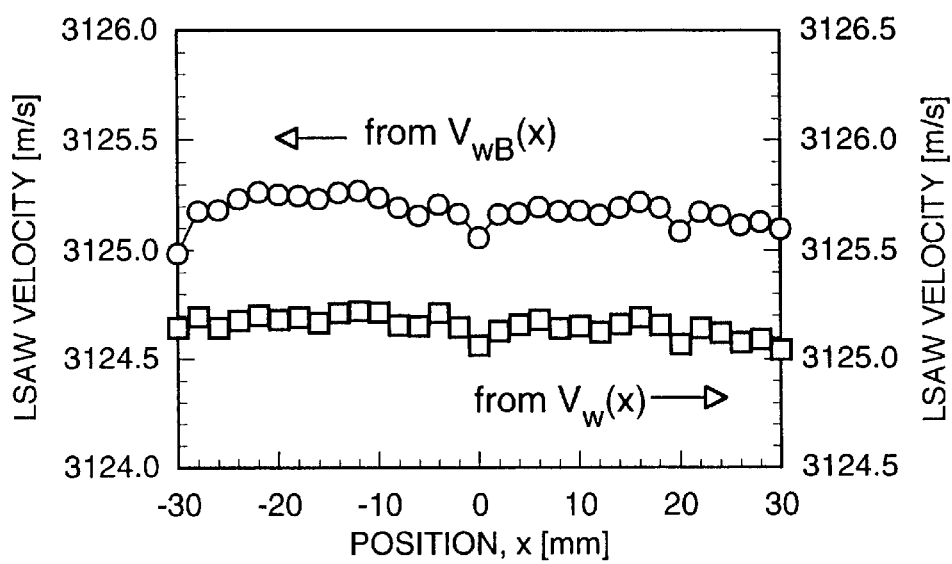
FIG. 23B is a graph showing measurement values of the LSAW velocity.
Figure 25A:
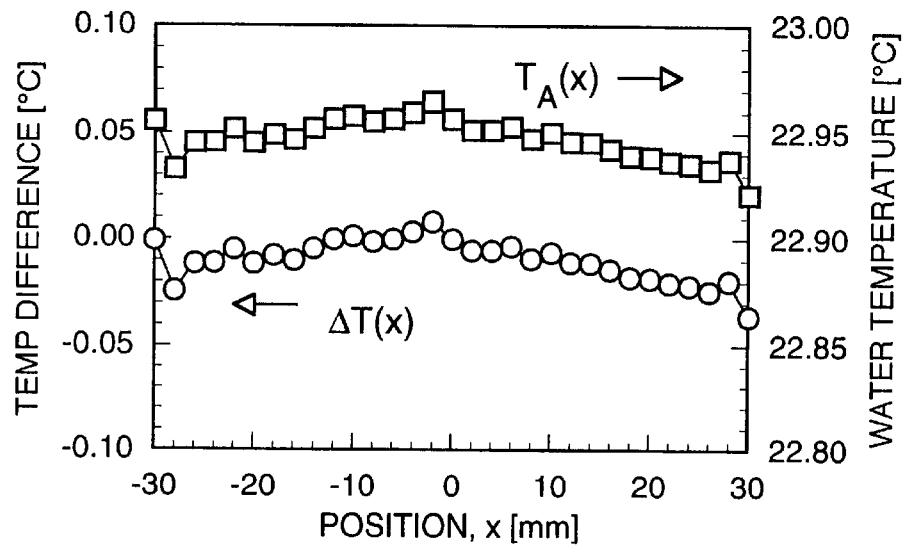
FIG. 25A is a graph showing the temperature difference $\Delta T(x)$ from the reference temperature $T_{A0}$ at each position x, calculated from $k_W'(x)$ in FIG. 24B, and $T_A(x)$ in the ultrasonic wave propagation region calculated from $\Delta T(x)$.
Figure 25B:
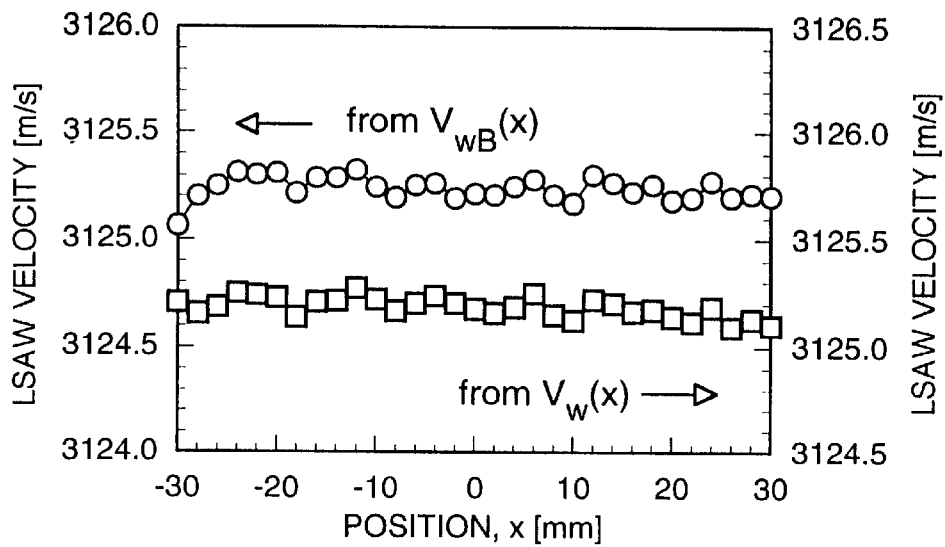
FIG. 25B is a graph showing measurement values of the LSAW velocity.

Incidentally, the variation $\Delta T(x)$ in the water temperature $T_A(x)$ from the reference value $T_{A0}$ is −0.019 to 0.007° C. in the complex V(z) curve measurement and −0.036 to 0.008° C. in the amplitude V(z) curve measurement as can be seen from FIGS. 23A and 25A. Accordingly, in this case, even if the reference temperature $T_{A0}=22.957°$ C. measured at the center on the specimen surface is used as $T_A(x)$, the maximum temperature measurement error is 0.019° C. in the complex V(z) curve measurement and 0.036° C. in the amplitude V(z) curve measurement. These values correspond to LSAW velocity measurement errors 0.0019% and 0.0036%, respectively. Hence, when the variation in the water temperature $T_A(x)$ derived from the V(z) curve is small, even if $T_{A0}$ is used as the water temperature, the LSAW velocity can be obtained within an estimated error range.

EFFECT OF THE INVENTION

According to the present invention, it is possible to clarify the water temperature distribution that is unknown in the prior art and depends on the quantity of water, surface configuration of water, specimen, configuration of the specimen, measurement temperature environment, measurement conditions, ultrasonic device configuration, or characterization system used. Thus, by starting the measurement at one fixed point on the specimen surface after the water temperature distribution becomes stable, the temperature in the ultrasonic wave propagation region in the water can be measured with high accuracy through utilization of the temperature compensating parameter.

Further, under measurement conditions where the water temperature distribution undergoes a substantial change as in the measurement of the two-dimensional LSAW velocity distribution, changes in the temperature and the longitudinal wave velocity at each position on the specimen surface can be accurately detected using the wave number of the longitudinal wave in the ultrasonic wave propagation region which is derived from the measured V(z) curve. When the temperature variation at each position is small, even if the fixed temperature detected at the reference point is used, the LSAW velocity can be measured within an estimated error range.

It is considered that the water temperature distribution differs with conditions such as the translation speed of the XY stage and the time until the start of the V(z) curve measurement after the translation, but in such an instance, too, variations in temperature and the longitudinal wave velocity can be detected with high accuracy. This provides increased accuracy in the measurement of the LSAW propagation characteristics, permitting high accuracy analysis and evaluation of material properties by the ultrasonic material characterization system. Conventionally, the measurement conditions are determined empirically to keep the quantity of water constant, but the present invention enables an arbitrary quantity of water to be used according to the contents of measurement without impairing the measurement repeatability.

In the above, the present invention has been described as being applied to the measurement of the two-dimensional LSAW velocity distribution under conditions where the water temperature distribution changes, the invention is also applicable, of course, to long-time measurements during which the water temperature distribution changes due to a decrease in the quantity of water by its evaporation. The present invention can be applied equally as well to measurements using the point-focus ultrasonic beam (PFB) and using acoustic couplers other than water. It is also possible to determine the water temperature and the longitudinal velocity through utilization of the wave number of the longitudinal wave that is derived, on the same principle as described above, from a V(f) curve obtained by sweeping the frequency f, with the distance z between the acoustic lens and the specimen fixed.

References (1) J. Kushibiki and N. Chubachi, "Material characterization by line-focus-beam acoustic microscope," IEEE Trans. Sonics and Ultrason., Vol. SU-32, pp. 189–212 (1985).
(2) "Ultrasonic Microscope System for Quantitative Measurement" (Japanese Pat. Laid-Open Gazette No. 281634/99).
(3) W. Kroebel and K.-H. Mahrt, "Recent results of absolute sound velocity measurements in pure water and sea water at atmospheric pressure," Acustica, Vol. 35, pp. 154–164 (1976).
(4) J. Kushibiki, Y. Ono, and I. Takanaga, "Ultrasonic micro-spectroscopy of $LiNbO_3$ and $LiTaO_3$ single crystals for SAW devices," Trans. IEICE C-I, Vol. J82-C-I, pp. 715–727 (1999).
(5) J. Kushibiki and M. Arakawa, "A method for calibrating the line-focus-beam acoustic microscopy system," IEEE Trans. Ultrason., Ferroelect., Freq. Contr., Vol. 45, pp. 421–430 (1998).

What is claimed is:

1. An LSAW propagation characteristics measuring method in which: a specimen under examination is irradiated with a focused ultrasonic beam by an acoustic lens through water used as an acoustic coupler; variations in an interference signal, which is a reflected signal from said specimen, with the relative distance z between an ultrasonic device and said specimen is obtained as a V(z) curve that is a function of said z; and said V(z) curve is analyzed to obtain the phase velocity and propagation attenuation that are propagation characteristics of a leaky surface acoustic wave (LSAW), said method comprising the steps of:

(a) pre-measuring, for said specimen, the water temperature $T_{AM}$ in a region directly below the surface of said acoustic lens and the water temperature $T_{BM}$ in a region near said acoustic lens to detect the temperature difference $\Delta T_M$;

(b) measuring said V(z) curve at the same time as the measurement of said water temperature $T_{BM}$ and obtaining an interference interval $\Delta z$ with respect to said z;

(c) estimating, for said specimen, the water temperature $T_{AM}$ in said region directly below the surface of said acoustic lens, and determining the longitudinal wave velocity $V_W$ in said water at said estimated temperature $T_{AM}$ based on a known data table; and (d) calculating the velocity $V_{LSAW}$ of said leaky surface acoustic wave from said determined longitudinal wave velocity $V_W$, said interference interval $\Delta z$, and an ultrasonic frequency f.

2. The method of claim 1, wherein said step (b) includes a step of calculating an interference wave number $k(\Delta z)$ by FFT based on said V(z) curve, and deriving said interference interval $\Delta z$ from said interference wave number $k(\Delta z)$.

3. The method of claim 1, wherein said step (c) includes a step in which: in the case of a measurement at one arbitrary fixed point on the surface of said specimen in stable temperature environments, a temperature difference $\Delta T_S$ between a temperature $T_{AS}$ in said region near said acoustic lens and a temperature $T_{BS}$ in said region directly below the surface of said acoustic lens is detected for a standard specimen; and if said temperature difference $\Delta T_S$ is nearly equal to said temperature difference $\Delta T_M$ within a predetermined error range, said water temperatures $T_{BM}$, $T_{BS}$ for said specimen under examination and said standard specimen are regarded as said water temperatures $T_{AM}$, $T_{AS}$ for said specimen under examination and said standard specimen, respectively, and if not, calculating $T_{AMB}=T_{BM}+\Delta T_M$ and $T_{AS}=T_{BS}+\Delta T_S$ for said specimen under examination and said standard specimen, respectively.

4. The method of claim 3, further including a step of repeating the calculation of a longitudinal wave number $k_{W}'$ by an FFT analysis of said V(z) curve measured at said one arbitrary fixed point until said wave number becomes substantially constant within a predetermined range to thereby make sure that said water temperature $T_{AM}$ in said region directly below the surface of said acoustic lens is stable.

5. The method of claim 1, wherein: said step (c) comprises the steps of:

(c-1) measuring a V(z) curve at a reference position (0, 0) in said region directly below the surface of said acoustic lens, and calculating a longitudinal wave number $k_{W0}'$ by FFT from said V(z) curve measured at the reference position (0, 0);

(c-2) measuring a V(z) curve at an arbitrary position (x, y) in said region directly below the surface of said acoustic lens, and calculating a longitudinal wave number $k_{W}'(x, y)$ from said V(z) curve measured at said arbitrary position (x, y); and (c-3) reading out of said known data table the longitudinal wave velocity $V_{W0}$ corresponding to a water temperature $T_{A0}$ at said reference position, calculating a difference $\Delta V_W(x, y)$ between said longitudinal wave velocity $V_{W0}$ at said reference position and the longitudinal wave velocity $V_W(x, y)$ at said arbitrary position from said wave numbers $k_{W0}'$ and $k_W'(x, y)$, and obtaining the longitudinal wave velocity at said arbitrary position (x, y) as $V_W(x, y)=V_{W0}+\Delta V_W(x, y)$; and said step (d) includes a step of obtaining said leaky surface acoustic wave velocity $V_{LSAW}$ from said longitudinal wave velocity $V_W(x, y)$, said interference interval $\Delta z$, and said ultrasonic frequency f.

6. The method of claim 5, wherein said step (c-3) comprises the steps of:

(c-3-1) reading out of said known data table the rate of change, $dV_W/dT$, of said longitudinal wave velocity $V_W$ to temperature, and estimating, by calculation, a temperature difference $\Delta T(x, y)$ between the temperature at said reference position (0, 0) and the temperature at said arbitrary position (x, y) from said wave numbers $k_{W0}'$ and $k_W'(x, y)$; and (c-3-2) reading out of said known data table said longitudinal wave velocity $V_{W0}$ corresponding to said water temperature $T_{A0}$ at said reference position (0, 0), calculating said difference $\Delta V_W(x, y)$ between said longitudinal wave velocity $V_{W0}$ at said reference position (0, 0) and the longitudinal wave velocity $V_W(x, y)$ at said arbitrary position (x, y) from said temperature difference $\Delta T(x, y)$ and said rate of change $dV_W/dT$, and obtaining the longitudinal wave velocity $V_W(x, y)$ at said arbitrary position (x, y) as $V_W(x, y)=V_{W0}+\Delta V_W(x, y)$.

7. The method of claim 6, wherein said temperature difference $\Delta T(x, y)$ in said step (c-3-1) is calculated by the following equation $$\Delta T(x, y) = \frac{2\pi f\{k_{W0}' - k_W'(x, y)\}}{k_{W0}'k_W'(x, y)\frac{dV_W}{dT}}$$

and said velocity difference $\Delta V_W(x, y)$ in said step (c-3-2) is calculated by the following equations $$V_W(x, y)=V_{W0}+\Delta V_W(x, y)$$

$$\Delta V_W(x, y) = \frac{dV_W}{dT} \cdot \Delta T(x, y).$$

8. The method of claim 5, wherein said velocity difference $\Delta V_W(x, y)$ in said step (c-3) is calculated by the following equation $$\Delta V_W(x, y) = V_W'(x, y) - V_{W0}' = \frac{2\pi f\{k_{W0}' - k_W'(x, y)\}}{k_{W0}'k_W'(x, y)}.$$

9. The method of any one of claims 6 and 7, wherein in a two-dimensional distribution measurement, when said temperature difference $\Delta T(x, y)$ obtained from said $k_{W0}'$ and $k_W'(x, y)$ is smaller than a predetermined value, the temperature measured at said reference point (0, 0) is used as said water temperature $T_{A0}$.

10. The method of any one of claims 3 and 4, which further comprises a step of measuring a V(z) curve for said standard specimen, and deriving an absolute calibration coefficient from the V(z) curve measured for said standard specimen, and wherein said step (d) is a step of calibrating said interference interval $\Delta z$ by said absolute calibration coefficient, and calculating said leaky surface acoustic wave velocity through the use of said calibrated $\Delta z$.

11. The method of any one of claims 1 to 8, wherein the measurement of said V(z) curve for said specimen to be examined is to measure the amplitude of said interference signal.

12. The method of any one of claims 1 to 8, wherein the measurement of said V(z) curve for said specimen to be examined is to measure the amplitude and phase of said interference signal.

13. The method of any one of claims 1 to 8, wherein the measurement of said V(z) curve for said specimen to be examined is to measure the complex quantities of said interference signal.

14. An LSAW propagation characteristics measuring apparatus which: applies a ultrasonic beam generated by a transducer to a specimen under examination by an acoustic lens through water used as an acoustic coupler; obtains variations in a reflected signal from said specimen with the relative distance z between an ultrasonic device and said specimen, as a V(z) curve that is a function of said z; and analyzes said V(z) curve to obtain the phase velocity and propagation attenuation that are propagation characteristics of a leaky surface acoustic wave (LSAW), said apparatus comprising:

receiving means for receiving a signal from said transducer to derive therefrom an interference signal V(z);

analysis means for analyzing said interference signal V(z) from said receiving means to obtain said LSAW propagation characteristics; and temperature measuring means for measuring the water temperature in the vicinity of said acoustic lens and in a region directly below the surface of said acoustic lens;

wherein said analysis means comprises means for calculating a temperature difference $\Delta T_M$ between the water temperature $T_{BM}$ in the vicinity of said acoustic lens and the water temperature $T_{AM}$ in said region directly below the surface of said acoustic lens pre-measured for said specimen under examination, and for estimating a water temperature $T_{AM}$ in said region directly below the surface of said acoustic lens by $T_{AM}=T_{BM}+\Delta T_M$ during measurement of said interference signal V(z) of said specimen under examination to remove a measurement error by said temperature difference $\Delta T_M$.

15. The apparatus of claim 14, wherein said receiving means includes means for measuring the amplitude of said V(z) curve.

16. The apparatus of claim 14, wherein said receiving means includes means for measuring the amplitude and phase of said V(z) curve.

17. The apparatus of claim 14, wherein said receiving means includes means for measuring the complex quantities of said V(z) curve.

18. The apparatus of any one of claims 14 to 17, further comprising means for calculating, through the use of a temperature compensating parameter, the temperature in an ultrasonic wave propagation region from a temperature measurement value in a temperature monitoring region during the measurement of said V(z) curve.

19. The apparatus of any one of claims 14 to 17, further comprising means for maintaining the quantity of said water more than a fixed value to provide a constant temperature difference between said water temperature in the vicinity of said acoustic lens and said water temperature in said region directly below the surface of said acoustic lens.

20. The apparatus of claim 19, wherein said quantity of said water is more than 0.5 cc.

21. The apparatus of claim 19, wherein said quantity of said water is 0.6 to 1.2 cc.

22. The apparatus of 19, wherein said means for maintaining the quantity of water is means for maintaining the quantity of water by periodically supplying said water into between said acoustic lens and said specimen.

23. The apparatus of claim 14, wherein said analysis means includes means for deriving the wave number of a longitudinal wave in an ultrasonic wave propagation region in said water from a complex V(z) curve having amplitude/phase information.

24. The apparatus of claim 14, wherein said analysis means includes means for deriving the wave number of a longitudinal wave in an ultrasonic wave propagation region in said water from a complex V(z) curve having only amplitude information.

25. The apparatus of claim 24, wherein said analysis means includes means for deriving the wave number of a longitudinal wave in said ultrasonic wave propagation region in said water through utilization of the interference between a carrier leakage signal in an RF switching circuit for generating an RF tone burst signal and said interference signal V(z).

26. The apparatus of claim 24, wherein said analysis means includes means for deriving the wave number of a longitudinal wave in said ultrasonic wave propagation region in said water by an electric interference method that causes interference between said interference signal V(z) and a continuous wave reference signal.

27. The apparatus of claim 14, wherein said analysis means includes means for obtaining the wave number of a longitudinal wave in said region directly below the surface of said acoustic lens in said water from phase information of said V(z) curve.

* * * * *